United States Patent
Whitaker et al.

(10) Patent No.: US 6,284,473 B1
(45) Date of Patent: *Sep. 4, 2001

(54) P-CRESOL SULFATE, A COMPONENT OF URINARY MYELIN BASIC PROTEIN-LIKE MATERIAL, AS A CORRELATE OF MULTIPLE SCLEROSIS STATUS

(75) Inventors: John Nicholas Whitaker; Robert David Kachelhofer; Edwin Luther Bradley, Jr., all of Birmingham, AL (US); Sheila Loughran Burgard, Lake Bluff, IL (US); Beverly Ann Layton, Birmingham, AL (US); Anthony Thomas Reder, Oak Park, IL (US); Wendy Jean Morrison, Vancouver (CA); Guojun Zhao, Burnaby (CA); Donald Winston Paty, Vancouver (CA); Ligong Cao; Lori Coward, both of Birmingham, AL (US); Patricia L. Jackson, Moody, AL (US); Marion Kirk, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,851

(22) Filed: Oct. 6, 1999

Related U.S. Application Data

(63) Continuation-in-part of application No. 08/723,581, filed on Oct. 1, 1996, now Pat. No. 5,998,150.
(60) Provisional application No. 60/004,659, filed on Oct. 2, 1995.

(51) Int. Cl.[7] .................. G01N 33/53; G01N 33/566; G01N 33/567; G01N 33/536

(52) U.S. Cl. .................. 435/7.1; 436/501; 436/504; 436/536; 436/540; 436/542; 436/804; 436/811

(58) Field of Search .................. 435/7.1; 436/501, 436/506, 536, 540, 542, 804, 811

(56) References Cited

U.S. PATENT DOCUMENTS 5,998,150 * 12/1999 Whitaker et al. .................. 435/7.1

OTHER PUBLICATIONS

Baumhefiner et al 1995 (Annals of Neurology, Aug., 38(2):315, Abstract No. M120).*

Whitaker (Annals of Neurology, 31 (3):346–348, Mar. 1992.*

Whitaker et al (Annals of Neurology, 35 (5):577–585, May 1994).*

* cited by examiner

*Primary Examiner*—Lynette R. F. Smith
*Assistant Examiner*—Padma Baskar
(74) *Attorney, Agent, or Firm*—Benjamin Aaron Adler

(57) ABSTRACT

The present invention provides a method of determining the status of a multiple sclerosis patient, i.e., predicting the transition from a status of relapsing-remitting to a progressive phase of multiple sclerosis, comprising the step of measuring the amount of urinary p-cresol sulfate in the patient. The present invention also provides a method of determining the amount of lesions and total lesion area of a multiple sclerosis patient, comprising the step of measuring the amount of urinary p-cresol sulfate in the patient. Further provided is a method of monitoring myelination in a developing child, comprising the step of: measuring the amount of p-cresol sulfate in the urine of said child.

19 Claims, 20 Drawing Sheets

P-CRESOL SULFATE, A COMPONENT OF URINARY MYELIN BASIC PROTEIN-LIKE MATERIAL, AS A CORRELATE OF MULTIPLE SCLEROSIS STATUS

CROSS REFERENCE RELATED APPLICATION

This application is a continuation-in-part application of Ser. No. 08/723,581 U.S. Pat. No. 5,998,150, filed Oct. 1, 1996, which claims benefit of priority under 35 USC §119(e) of U.S. provisional application No. 60/004,659, filed Oct. 2, 1995, now abandoned.

BACKGROUND OF THE INVENTION

1. Field of the Invention

The present invention relates generally to the field of neurology and multiple sclerosis. More specifically, the present invention relates to an assay for measuring urinary myelin basic protein-like material, more particularly the urinary p-cresol sulfate component, and the use of this assay as a correlate of multiple sclerosis status.

2. Description of the Related Art

Multiple sclerosis (MS), an inflammatory, primary demyelinating disease of the central nervous system (CNS) affecting an estimated 350,000 persons in the United States (1), is typified by a chronic and unpredictable course. This variable course and the associated heterogeneity of the disease renders clinical trials involving large groups and clinical management of the individual patient problematic. Based on disease course, multiple sclerosis patients are usually categorized (2,3) as relapsing-remitting (RR), relapsing progressive (RP), primary progressive (PP) and secondary progressive (SP), according to the clinical appearance and persistence of neurological deficit. The development of disease progression, whether from onset, as in PP-MS, or as SP-MS subsequent to an earlier period of relapses, can be viewed as the failure of remission. The failure of remission (i.e., progression of the disease) is the principal cause of disability and decline in the quality of life.

The natural history of MS has been studied extensively for clinical features or laboratory measurements which might predict, anticipate or parallel the future course of disease. Clinical characteristics which appear to predict a future progressive course include: (a) male gender; (b) later age of onset of the disease; (c) corticospinal and cerebellar involvement; (d) increased number of relapses in the first five years; and (e) shorter interval between the first and second relapse (2–4). The clinical scales for assessing progression of disability have certain limitations (5), but, in general, the functional status in a population of MS patients is better than usually envisioned (6), and patients, even with chronic progressive disease, may go through periods of spontaneous stability (7). This imprecision in clinical patterns and natural history requires clinical markers for signaling progression (8).

Several laboratory methods, including HLA typing (9) and cerebrospinal fluid (CSF) levels of tumor necrosis factor-a (10) have been reported to predict or parallel subsequent disease course in multiple sclerosis. Confirmation of these reported relationships have either not been successful (11) or conflicting (2). Serial cranial MRI, with or without gadolinium, represents another measure of clinical disease activity in MS (5, 12). Cranial MRI may predict the development of MS after initial signs (13) serve as a presumed surrogate marker in early MS (14) and cranial MRI demonstrates increasing lesion burden with longer duration of disease (12). The cranial MRI findings which are indicative of a chronic progressive course or which mark the transition from relapsing-remitting to chronic progressive disease are uncertain (15). Newer MRI techniques, such as magnetization transfer (16), may more accurately demonstrate the physiological changes of chronic progressive-multiple sclerosis. Whatever the technique, cranial MRI furnishes an incomplete record about the change to a chronic progressive course since such change often involves the spinal cord.

Given the encephalitogenic properties of myelin basic protein (MBP) for inducing experimental allergic encephalomyelitis (EAE), a model of multiple sclerosis (MS), MBP has been extensively characterized immunologically. Human MBP is encoded by a single gene comprising seven exons on human chromosome 18, where it resides on the 3' side of the larger golli-mbp gene (41). Due to alternate splicing of the seven exons, MBP may appear in at least five isoforms, with an 18.5 Kd molecule comprising 170 amino acid residues predominating in central nervous system (CNS) myelin of adults (42). Extensive post-translational modification of MBP results in many charge isomers, such that MBP is comprised of a family of molecules (43). MBP has many epitopes for T and B cells, which, for B cells, conform to a flexible model (44). Some of the B cell epitopes, notably those in the carboxyl residues of MBP peptide 80–89, are cryptic and not expressed in the intact molecule of MBP (45).

Myelin basic protein (MBP) comprises 30% of CNS myelin proteins (17). Material, designated as myelin basic protein-like material (MBPLM), i.e., reactive with antibodies to myelin basic protein, normally exists at very low levels in CSF but increases after acute CNS myelin damage (18, 19). Serial sampling of CSF is not feasible, but the level of CSF myelin basic protein-like material in a multiple sclerosis patient with recent clinical worsening is predictive of a response to a regimen of intravenous methylprednisolone and oral prednisone (20). CSF myelin basic protein-like material has a molecular weight of >30,000 and appears to be bound to a carrier molecule (21). Myelin basic protein-like material in CSF is best recognized by an antibody reactive with an epitope that is conformationally present in the intact myelin basic protein molecule and represented by residues 80–89.

Urinary myelin basic protein-like material, usually found in low levels in normal individuals, is present in elevated levels in certain multiple sclerosis patients and is quite different in size and immunochemical features from the myelin basic protein-like material present in CSF (22). Urinary MBPLM has a molecular weight of <1000, is not bound to any other substances and appears to be similar to myelin basic protein residues 83–89 (22, 23). The level of urinary myelin basic protein-like material, unlike the level of myelin basic protein-like material in CSF, does not reflect acute disease activity in multiple sclerosis and correlates best with the existence of chronic progressive disease (23).

Recombinant interferon beta-1b (IFNβ-1b) is the first therapeutic agent which can alter the natural history of relapsing-remitting multiple sclerosis by reducing the number and severity of relapses and the volume of white matter detected by cranial MRI (24). Although disease progression was not an end point in that trial of IFNβ-1b, there was a non-significant trend toward an effect of treatment on disease progression (24). Although not FDA-approved, IFNβ-1b has been shown in a European study to reduce progression in SP-MS (Kappos et al Lancet November, 1998).

Thus, the prior art is deficient in the lack of effective means of determining the failure of remission and/or diagnosing the presence of a progressive phase in patients having multiple sclerosis.

The present invention fulfills this longstanding need and desire in the art.

SUMMARY OF THE INVENTION

In the multi-center, randomized placebo-controlled trial of alternate-day injections of recombinant interferon beta-1b (IFNβ-1b) in relapsing-remitting (RR) multiple sclerosis, urine specimens were collected periodically from all patients (n=64) in two of the clinical test sites over the two years of the study. Urine was also collected over two consecutive 24 hour periods from 43 patients from a third center. Urine samples were assayed for their content of myelin basic protein-like material, the level of which was correlated with a variety of clinical changes, cranial MRI results and the development of progressive disease. The level of urinary myelin basic protein-like material correlated with a secondary progressive (SP) course and with the number and total area of lesions on T2-weighted cranial MRI. A rise in the level of urinary myelin basic protein-like material antedates the clinical transition from a relapsing-remitting to a chronic progressive course. The randomized entry of patients led to significant differences in urinary myelin basic protein-like material among the three treatment groups, thus precluding correlation studies of treatment effects. However, the patient group from which the 24 hour specimens were collected showed that the relapsing-remitting multiple sclerosis patients changing to a chronic progressive course had the highest values of urinary myelin basic protein-like material.

The present invention further identifies p-cresol sulfate as the major component of urinary MBPLM. This conclusion is based upon the following: 1) MBPLM and p-cresol sulfate both have a mass of 187 on negative scans by electrospray ionization mass spectrometry, and the same species of 80 ($SO_3^-$) and 107 (methylphenol) mass units were observed on tandem mass spectrometry with similar profiles on multiple reaction monitoring; 2) $^1H$ and $^{13}C$ nuclear magnetic resonance spectroscopy revealed identical spectra for MBPLM and p-cresol sulfate; 3) purified cresol sulfate reacted in parallel with MBP peptide 83–89 in the same radioimmunoassay for MBPLM; and 4) p-cresol sulfate had the same behavior on preparative HPLC columns as urinary MBPLM.

Thus, the present invention demonstrates that urinary myelin basic protein-like material, and more specifically, urinary p-cresol sulfate, offers an objective test and can serve as a surrogate marker in urine for detecting or predicting the failure of remission or the transition to a progressive phase of multiple sclerosis.

In one embodiment of the present invention, there is provided a method of predicting the transition from relapsing-remitting multiple sclerosis to progressive multiple sclerosis in a patient with multiple sclerosis, comprising the steps of: (a) collecting multiple urine samples over time from a patient with multiple sclerosis; (b) measuring the amount of p-cresol sulfate in the urine samples; and (c) comparing the amount of the p-cresol sulfate in each urine sample from the patient to an art-accepted standard; wherein an increase over time in the urinary p-cresol sulfate levels in the urine samples is predictive of the transition from the relapsing-remitting multiple sclerosis to the progressive phase of multiple sclerosis in the patient.

In another embodiment of the present invention, there is provided a method of predicting an increase in the amount of lesions and/or total lesion area of a patient with multiple sclerosis, comprising the steps of: (a) collecting multiple urine samples over time from a patient with multiple sclerosis; (b) measuring the amount of p-cresol sulfate in the urine samples; and (c) comparing the amount of the p-cresol sulfate in each urine sample from the patient to an art-accepted standard; wherein an increase in the p-cresol sulfate level in the urine samples is predictive of an increase in the amount of lesions and/or total lesion area in the patient.

In yet another embodiment of the present invention, there is provided a method of predicting normal age-related changes in myelination in a developing child, comprising the steps of: (a) collecting multiple urine samples over time from a child; (b) measuring the amount of p-cresol sulfate in the urine samples; and (c) comparing the amount of the p-cresol sulfate in each urine sample from the child to an art-accepted standard; wherein from birth through approximately one year of age, the amount of urinary p-cresol sulfate is lower in the child relative to established values for adults; wherein from approximately one year of age through approximately five years of age, the amount of urinary p-cresol sulfate in the child increases linearly exceeding the established values for adults; wherein between approximately five years of age and approximately eight years of age, the amount of urinary p-cresol sulfate in the child decreases to approximately established values for adults; wherein the amount of urinary p-cresol sulfate in the child is predictive of normal age-related changes in the developing child.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention, and therefore, are not to be considered limiting in their scope.

DETAILED DESCRIPTION OF THE INVENTION

Figure 1:
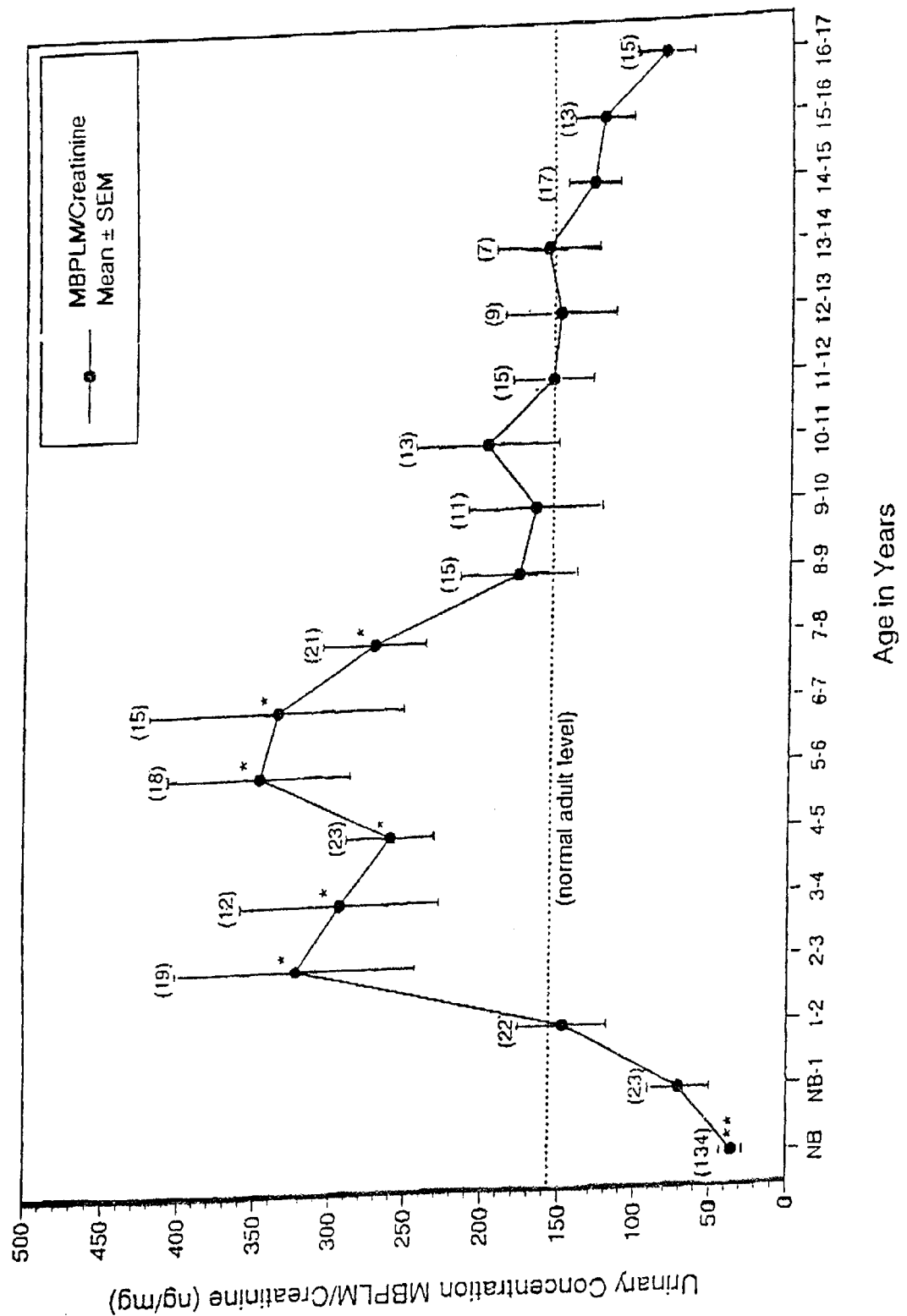
FIG. 1 shows human urinary MBPLM levels, expressed as ng/mg creatinine, from birth (newborn or NB) to 17 years of age. These levels are significantly lower ** ($p<0.05$) in newborns and significantly higher * ($p<0.05$) in the groups from 2–3 years through 7–8 years of age than the normal adult level of 157.3±83.9 ng MBPLM/mg creatinine (see horizontal line).

Multiple sclerosis (MS) is an inflammatory, demyelinating and chronic disease of the human central nervous system. It is clinically heterogeneous and follows an unpredictable course. A high priority for more effective treatment of MS is an objective and feasible laboratory test for predicting the disease's course and response to treatments. Urinary myelin basic protein (MBP)-like material (MBPLM), so designated because it is immunoreactive as a cryptic epitope in peptide 83–89 of the human MBP molecule of 170 amino acids, is present in normal adults, remains normal in relapsing-remitting MS, but increases in the progressive phases of MS.

In addition to demonstrating a correlation between urinary MBPLM and the transition to progressive phases of multiple sclerosis, the present investigation describes the purification and characterization of urinary MBPLM. p-Cresol sulfate is the major component of urinary MBPLM. This conclusion is based upon the following: 1) MBPLM and p-cresol sulfate both have a mass of 187 on negative scans by electrospray ionization mass spectrometry, and the same species of 80 ($SO_3^-$) and 107 (methylphenol) mass units were observed on tandem mass spectrometry with similar profiles on multiple reaction monitoring; 2) $^1H$ and $^{13}C$ nuclear magnetic resonance spectroscopy revealed identical spectra for MBPLM and p-cresol sulfate; 3) purified cresol sulfate reacted in parallel with MBP peptide 83–89 in the same radioimmunoassay for MBPLM; and 4) p-cresol sulfate had the same behavior on preparative HPLC columns as urinary MBPLM.

The present invention is directed towards a method of predicting the transition from relapsing-remitting multiple sclerosis to progressive multiple sclerosis in a patient with multiple sclerosis, comprising the steps of: (a) collecting multiple urine samples over time from a patient with multiple sclerosis; (b) measuring the amount of p-cresol sulfate in the urine samples; and (c) comparing the amount of the p-cresol sulfate in each urine sample from the patient to an art-accepted standard; wherein an increase over time in the urinary p-cresol sulfate levels in the urine samples is predictive of the transition from the relapsing-remitting multiple sclerosis to the progressive phase of multiple sclerosis in the patient.

The present invention is further directed towards a method of predicting an increase in the amount of lesions and/or total lesion area of a patient with multiple sclerosis, comprising the steps of: (a) collecting multiple urine samples over time from a patient with multiple sclerosis; (b) measuring the amount of p-cresol sulfate in the urine samples; and (c) comparing the amount of the p-cresol sulfate in each urine sample from the patient to an art-accepted standard; wherein an increase in the p-cresol sulfate level in the urine samples is predictive of an increase in the amount of lesions and/or total lesion area in the patient.

The present invention is additionally directed towards a method of predicting normal age-related changes in myelination in a developing child, comprising the steps of: (a) collecting multiple urine samples over time from a child; (b) measuring the amount of p-cresol sulfate in the urine samples; and (c) comparing the amount of the p-cresol sulfate in each urine sample from the child to an art-accepted standard; wherein from birth through approximately one year of age, the amount of urinary p-cresol sulfate is lower in the child relative to established values for adults; wherein from approximately one year of age through approximately five years of age, the amount of urinary p-cresol sulfate in the child increases linearly exceeding the established values for adults; wherein between approximately five years of age and approximately eight years of age, the amount of urinary p-cresol sulfate in the child decreases to approximately established values for adults; wherein the amount of urinary p-cresol sulfate in the child is predictive of normal age-related changes in the developing child. Typically, the child has a demyelinating condition.

Representative means of measuring include a radioimmunoassay, NMR spectroscopy (both $^1$H and $^{13}$C), electrospray spectrometry and tandem mass spectrometry. Preferably, the radioimmunoassay is a double-antibody radioimmunoassay, and more preferably, the double-antibody radioimmunoassay uses rabbit antiserum 110 (R110), radioiodinated myelin basic protein residues 45–89, or fragments thereof (preferably, residues 69–89), as a radioligand, myelin basic protein residues 83–89 as a radioimmunoassay standard and goat, anti-rabbit IgG as a second antibody.

Typically, the art-accepted standard for the comparison is selected from the group consisting of urinary creatinine levels in each the sample, urinary volume of each the sample and total urinary volume collected over a defined period of time. Oftentimes, the defined period of time is 24 hours.

The following examples are given for the purpose of illustrating various embodiments of the invention and are not meant to limit the present invention in any fashion.

EXAMPLE 1
Patients and Treatment Groups

From the population of 372 adult multiple sclerosis patients, all relapsing-remitting (RR) at the beginning of the study, entered in the Betaseron® (Interferon beta-1b or IFNβ-1b) therapeutic trial (24), a total of 107 patients from three of the 11 study sites were included. The Institutional Review Boards at the three study sites approved the investigations conducted. The patient population consisted of 12 patients from the University of Alabama at Birmingham (UAB), 52 patients from the University of British Columbia (UBC) and 43 patients from the University of Chicago. The patients were randomly and equally divided among three treatment groups which received placebo, 1.6 million IU (0.05 mg) or 8 million IU (0.25 mg) of IFNβ-1b subcutaneously on alternate days. At the time of each clinic visit, patients were examined and assigned a Kurtzke Expanded Disability Status Scale score (EDSS) (25) and a Scripps score (26). In addition to determining difference and percentage change in the EDSS and Scripps scores, the occurrence and timing of conversion from a relapsing-remitting to chronic progressive (chronic progressive) phase were noted. Progression was defined as a confirmed increase in EDSS of one point over baseline.

Urine was collected at entry and before randomization in the trial and then annually on all patients from UAB and UBC (Group 1). In addition the patients at UBC had urine collected at six week intervals (Group 2) on the same day on which they had a cranial MRI (12, 24). In the UBC cohort, nine of the 52 patients failed to have their initial urine specimens collected at the start of the clinical trial. Although the significance of the findings is not altered by inclusion or exclusion of these nine patients, the means, medians and statistical differences described are adjusted for the nine.

As part of a separate study at the University of Chicago on the effect of IFNβ-1b on the adrenal cortex and corticosteroid excretion (27), urine was collected over two consecutive 24 hour periods on 43 patients with relapsing-remitting multiple sclerosis. The length of time in the therapeutic trial at the time of sample collection ranged from 210 to 810 days. One of the collections was for the "on" day following IFNβ-1b administration, and the other was for the "off" day of the alternate day treatment regimen (24). A total of 85 specimens were available, 43 patients from the "on" day and 42 of the same 43 patients from the "off" day. Urine volume was determined (judged to be complete and accurate in 74 of the 85 collections), and a 15 ml aliquot was stored at −20° C. Of the 43 patients, 30 patients remained relapsing-remitting, i.e., nonprogressive, and 13 patients became progressive or chronic progressive. For the patient group with accurate 24 hour collection volumes, 27 patients remained relapsing-remitting and 10 patients became chronic progressive.

EXAMPLE 2
Reagents

Trifluoroacetic acid, Sequenal grade, was purchased from Pierce Chemical (Rockford, Ill.). Acetonitrile, ultraviolet grade, was obtained from Burdick and Jackson Laboratories (Muskegon, Mich.). Organic-free water for high-performance liquid chromatography (HPLC) was prepared by ultraviolet irradiation of Milli-Q (Millipore-Continental Water Systems, Bedford, Mass.) water in a Model 816 HPLC Reservoir (Photronix, Medway, Mass.). CM-SEPHADEX C-25 (crosslinked dextran) was purchased from Pharmacia Fine Chemicals (Piscataway, N.J.). Aprotinin (Trasylol) was purchased from Mobay Chemical (New York, N.Y.).

EXAMPLE 3
Preparation of MBP and MBP Peptides

MBP was isolated from bovine brain by delipidation, acid extraction at pH 3, and carboxymethylcellulose chromatography at pH 10.6. Components one to four were pooled, subjected to limited digestion with pepsin, and chromatographed on carboxymethylcellulose in 0.2 M ammonium bicarbonate (pH 7.6). The fraction, previously designated as PI, was isolated and shown to be a mixture (30:70 ratio) of bovine basic protein peptides 45–89 and bovine MBP peptide 43–88. Small peptides from human, bovine, and guinea pig MBP were prepared or synthesized as described.

EXAMPLE 4
Preparation of Immunogen

Eleven milligrams of the bovine MBP peptides in chromatograph fraction $P_1$ was combined with 11 mg of ovalbumin in 2.75 ml of distilled water and stirred at 25° C. 14 mg of 1-ethyl-3 (3-dimethyl-aminopropyl) carbodiimide hydrochloride was added and the stirring at 25° C. continued for 22 hours. The solution was then dialyzed at 4° C. against one liter of distilled water over 4 days; the dialysis bath was changed daily. The dialyzed material was then frozen and stored at −20° C.

EXAMPLE 5
Immunization Protocol

An emulsion was made by mixing 200 ul of the bovine MBP peptide-ovalbumin conjugate with 1.8 ml of 0.15 M NaCl and 2.0 ml of complete Freund's adjuvant supplemented with 10 mg of mycobacterium H37RA. This mixture was homogenized in Virtis 23 at high speed for 2 min at 25° C. The emulsion was used to immunize New Zealand white female rabbits (designated R110 and R111) weighing approximately 2.5 kg. Each animal received 0.25 ml in each footpad and 0.5 ml intradermally in 12 sites on each flank for a total of 2 ml per animal. Assuming 100% efficiency in conjugation, each animal received 800 mg of peptide linked to ovalbumin. One month later each animal received the same amount of peptide-ovalbumin conjugate with the emulsion made with incomplete Freund's adjuvant and with no additional mycobacterium. The injections were made intramuscularly in each hind leg and subcutaneously over the shoulders and flanks. 1 week later the animals were bled. 4 weeks after the boosting with immunogen-incomplete Freund's adjuvant, each animal received 1 ml of 0.15 M NaCl intraperitoneally, to which had been added 100 $\mu$g of peptide-ovalbumin conjugate (100 $\mu$g peptide-100 $\mu$g ovalbumin) in an effort to prevent anaphylaxis. The next day, each animal received 600 $\mu$g peptide-ovalbumin conjugate (600 $\mu$g peptide-600 $\mu$g ovalbumin) intravenously in 1 ml of 0.15 M NaCl. 1 week later, the animals were bled on alternate days for a total of 100 ml in 3 bleedings. 1 month after the first intraperitoneal injection, the intraperitoneal and intravenous injections were repeated. The animals were bled twice during the following week, and 1 month later, the intravenous injection was again repeated. The animals were bled 3 times the following week on alternate days for a total bleeding of 135 ml. This last bleeding, referred to as R110 GHI, is the serum used for the studies described herein.

EXAMPLE 6
Specimens

Urine was collected as cumulative 24 hour or individual specimens from an external or internal catheter or by voiding, and was placed at 4° C. without preservative for up to 24 hours and subsequently stored fresh at −20° C. Individual urine specimens were usually collected around 8:00 am. In two men with chronic progressive MS whose urine was collected during 4 hour segments over 96 hours, there was no consistent diurnal variation. Some urine samples were stored at −20° C. in the presence of 0.1% methylated bovine serum albumin (MBSA). Still other samples of urine were dialyzed for 24 hours at 4° C. against distilled water. Dialyzed normal urine was used to dilute the urine samples to be evaluated. Clinical conditions were designated independently of laboratory test. The diagnosis of MS was based on the Schumacher criteria. An exacerbation of MS was defined as the appearance of a new neurological deficit or the worsening of a previous one lasting 24 hours or longer and not explained by another cause.

Specimens of voided urine were obtained from 113 persons. These included 76 specimens from 26 normal control subjects, 59 specimens from 48 persons with other neurological diseases (OND), and 302 specimens from 39 persons with clinically definite MS. The OND group represented a variety of neurological disorders, including 8 patients who had had a stroke within 10 days of providing the urine specimen, 2 patients who had had a stroke one month or more previous to providing the specimen, 4 patients with various neurodegenerative diseases, 1 patient with sagittal sinus thrombosis, and 4 patients with headache or functional disorders.

EXAMPLE 7
Radioimmunoassay

A double antibody radioimmunoassay (DA-RIA) was performed at 4° C., with nonequilibrium conditions. Radio-iodination was by lactoperoxidase-catalyzed iodination. The final volume of the DA-RIA was 950 $\mu$l. On day one, 450 $\mu$l of 0.2 M Tris-acetate buffer (pH 7.2) containing 0.2% (w/v) MBSA (TA-MBSA) was placed in 12×75 mm plastic tubes and 200 $\mu$l of diluted first antibody was placed in a 1:200 dilution of normal rabbit serum in 0.2 M Tris-acetate buffer A (pH 7.2). Two different primary antibodies were used, but otherwise the assays were identical. The first antibody, R110, was used at a final dilution of 1:8,550. The second antibody, R79, was used at a final dilution of 1:3,800. 50 $\mu$l of MBP or MBP peptides in TA-MBSA or 50 ml of CSF or urine was used for evaluation. When less than 50 $\mu$l of body fluid was tested, it was mixed with enough TA-MBSA to give the sample a total volume of 50 $\mu$l. After 16 hours, 50 $\mu$l of TA-MBSA containing approximately 10,000 cpm of $^{125}$I-human MBP peptide 45–89 was added and allowed to stand for 20 hours. 200 $\mu$l of goat antirabbit IgG, diluted 1:4 in TA, was added. After 20 hours, the pellets were collected, washed, and counted on a gamma counter. Results of DA-RIA were charted by a logit-log method. For calculations of molar inhibitions, each amino acid residue in the protein or peptide was assigned a molecular weight of 100.

EXAMPLE 8
Processing of Urine Specimens Before HPLC 2 ml of urine was centrifuged at 3,000 rpm to remove any particulate matter and then adjusted to pH 5 with 1 M acetic acid and 0.1 M ammonium acetate (pH 5.0). This specimen was applied to a 0.7×2.5 cm column of CM-SEPHADEX C-25 (crosslinked dextran) that had been equilibrated with 0.02 M ammonium acetate (pH 5.0) and subsequently washed with 5 ml of the same buffer. All steps were performed at 25° C. The effluent (7 ml) was collected in one vial labeled "flow-through". Material that had bound to the column was eluted with 3.5 ml 1 M ammonium hydroxide. The eluate was collected in a vial and was immediately adjusted to pH 6 to 7 with 1 M acetic acid. 4 ml of water was added to the eluate, both flow-through and eluate were lyophilized twice and the residue was dissolved in 2 ml water. By DA-RIA, only the flow-through contained the urinary MBPLM, which was studied further by HPLC. The flow-through was chromatographed on a reverse-phase HPLC column.

EXAMPLE 9
HPLC

HPLC was performed on a Waters (Millipore, Waters Products Division, Milford, Mass.) liquid chromatograph equipped with two Model 6000A pumps, Model 660 solvent programmer, Model U6K injector, Model 450 variable-wavelength detector, and a Series B-5000 Omniscribe strip chart recorder (Houston Instrument, Austin, TX). A Vydac 218TP54 reversed-phase column ($C_{18}$, 25 cm×4.6 mm internal diameter, 5-mm particles), obtained from the Separation Group (Hesperia, Calif.), and a Waters guard column packed with Bondapak $C_{18}$/Corasil (Millipore) were used.

Solvent A was 0.1% (v/v) trifluoroacetic acid in water. Solvent B was 0.1% trifluoroacetic acid in a mixture of 9 parts acetonitrile to 1 part water. Solvents were prepared fresh daily and were filtered and degassed with nylon-66 membrane filters (0.45 mm pore size) purchased from Rainin Instrument (Woburn, Mass.). The composition of the mobile phase was adjusted using the solvent programmer with pure Solvent A from the A pump and pure Solvent B from the B pump.

The quantitative microcomplement fixation test was used. Urine was separated on SEPHADEX G-25 (dextran crosslinked with epechlorohydrin) equilibrated with 0.2 M $NH_4HCO_3$ at 4° C. 3 ml of urine was applied to a 1.5×90 cm column and 1 ml fractions were collected. Fractions from this were used for testing in the DA-RIA. Also, mixtures of the DA-RIA incubation and samples were chromatographed on SEPHADEX G-25 (dextran crosslinked with epechlorohydrin) in the presence or absence of urine containing MBPLM. In those determinations, the radioactivity of the eluted fractions was determined by gamma counting. Creatinine content in urine was measured with a kit assay (Sigma Chemical, St. Louis, Mo.) according to the prescribed protocol. Statistical evaluation was by comparison of means from independent samples and populations with unequal variances.

EXAMPLE 10
Quantitation of Urinary Myelin Basic Protein-Like Material

Urinary myelin basic protein-like material was quantitated with a double-antibody radioimmunoassay (RIA) using rabbit antiserum 110 (R110), radioiodinated myelin basic protein residues 45–89 as the radioligand and myelin basic protein residues 83–89 as the assay standard. The details and features of this radioimmunoassay are described above. The concentration of urinary myelin basic protein-like material was expressed as ng MBPLM/ml urine and also as ng MBPLM/mg creatinine (22). The concentration of urinary myelin basic protein-like material was also measured with two other radioimmunoassays in which either rabbit antiserum 3794 (R3794) or monoclonal antibody (mAb) F41 served as the first antibody, human myelin basic protein residues 69–89 served as the radioligand and the standard was human myelin basic protein residues 80–89. The characterization of reagents R3794 and mAb F41 and their use in quantitation of urinary myelin basic protein-like material by radioimmunoassay have been described (23).

EXAMPLE 11
Cranial MRI

Cranial MRI without gadolinium enhancement was performed according to specific protocol, and T2-weighted images were analyzed for Groups 1 and 2 (12). Cranial MRI at UBC was performed with a 0.15 T instrument, and those at UAB with a 1.0 T instrument. All MRI interpretations and measurements were made at UBC. For the cranial MRIs performed at UAB and UBC, the number of lesions identified (designated previously as regions of interest (12)), total lesion area and percent interval change in lesion area were determined. At UBC for the six week interval study, the number of new lesions, number of recurrent lesions, number of enlarging lesions, number of activity events and percent of active scans were determined (12, 24).

EXAMPLE 12
Data Analysis and Statistics

Analysis was performed on urine specimens from three patient groups. Group 1 (annual study) consisted of all annually collected specimens at UAB and UBC. Group 2 (six week study) were the specimens collected at six week intervals at UBC. Annual data on all patients were analyzed such that there were 168 urine specimens from individuals studied on the first visit (start of trial), second visit (one year after beginning) and third visit (two years after beginning), which were correlated with a total of 36 clinical and neuroimaging variables. For the study of the cohort from UBC (Group 2) on whom urine was collected at six week intervals, analysis was performed separately. Group 3 included 42 patients who had two consecutive 24 hour urine collections.

Continuous variables, such as urinary myelin basic protein-like material and creatinine, were summarized as mean+SD, and analyzed by a two-way (disease groups and visit) analysis of variance (ANOVA) with time treated as a repeated measures factor (28). Comparisons between disease groups at each visit and averaged over total visits used a two-tailed unpaired Student's t-test (29). Comparisons among treatment groups at each visit and averaged over visits used a one-way ANOVA (29). Multiple comparisons among pairs of means used the Fisher's protected least significant difference method (29). Associations between urinary myelin basic protein-like material values and MRI measurements were computed with Pearson's correlation coefficient (30). Comparisons of attribute data with disease groups or treatment groups used a Chi square test of proportions (31). The univariate associations of time until progression with the clinical and neurological variables utilized the log rank statistic (32) and the joint associations used Cox's proportional hazards model (33). Two-factor analysis of variance (34) was used to analyze the treatment and disease course simultaneously on the clinical and neurological variables. Covariance analysis was used to assess the effect of the length of time a subject was in the study on the results (34). When group standard deviations increased directly with the group means, data were subjected to logarithmic transformation and reanalyzed (28). Differences were declared statistically significant if $p<0.05$.

EXAMPLE 13
Urinary Myelin Basic Protein-Like Material

Two urine measurements expressed separately as myelin basic protein-like material (ng/ml) and creatinine (mg/ml) or as a combined value of myelin basic protein-like material/creatinine (ng/mg), to correct for variations in patient glomerular filtration function, were the bases for a variety of correlations. The general approach to analyzing the data was to search, first, for correlations overall during the study, and second, for predictive or parallel values of the measurements made at the beginning or at specified intervals. Since the urine measurements in Groups 1–3 had been an add-on to the clinical trial, some of the correlations could be viewed in a cautious fashion only as trends.

For the correlations overall, Groups 1 and 2 showed many similarities. The level of urinary myelin basic protein-like material correlated with both the number of lesions and the total lesion area detected by cranial MRI (Table 1). The data presented in Table 1 is expressed as a Pearson correlation coefficient and range of p-value for the sample size. Specific p-values are presented in this section. There was no correlation with the percent activity or the presence of new lesions by cranial MRI (Table 1). These relations implied, as had the results of a previous cross-sectional study (23), that the level of urinary myelin basic protein-like material did not correlate with active disease.

Levels of myelin basic protein-like material showed irregular correlations with disability scores. For Group 1, the level of myelin basic protein-like material correlated with EDSS score (p=0.0322). A concordant increase in creatinine resulted in no significance to the correlation of EDSS and myelin basic protein-like material/creatinine (p=0.6211). In Group 2, there was a significant correlation between myelin basic protein-like material, expressed either as a level or in relationship to creatinine, with EDSS score, and a significant indirect relationship with the Scripps score. When measurements overall or at selected times were analyzed, there were scattered correlations between MBPLM levels in urine and the number of lesions, the total lesion area detected by cranial MRI and the EDSS score (Table 1).

significant correlation for Group 2 (p=0.0001) (Table 2). These differences in the level of significance may be due to differences in sample size. There was an unexpected behavior exhibited for creatinine, which was higher concordantly with myelin basic protein-like material. For Group 1, but not for Group 2, this paralleling change in creatinine diminished the statistical significance of the correlations of myelin basic protein-like material with changes on cranial MRI (Table 1). For Group 2, there was a significant correlation (p=0.02 or

TABLE 1

Correlations Of Urinary Myelin Basic Protein-Like Material Variables With MRI And Clinical Measures

| | MRI | | | | Clinical | | |
|---|---|---|---|---|---|---|---|
| | Percent Activity | New Lesions | Number of Lesions | Total Area | EDSS | Scripps | Change to Prog. |
| Group 1 Overall (N = 168) | | | | | | | |
| Creatinine (mg/ml): | 0.128 | −0.009 | 0.182$^a$ | 0.230$^c$ | 0.201$^b$ | −0.210$^a$ | 0.172$^a$ |
| MBPLM (ng/ml): | 0.018 | −0.034 | 0.179$^a$ | 0.215$^c$ | 0.165$^a$ | −0.088 | 0.147 |
| MBPLM/Cr. (ng/mg): | −0.103 | −0.095 | 0.113 | 0.133 | 0.038 | −0.003 | 0.102 |
| Group 1 Visit 1 (N = 55) | | | | | | | |
| Creatinine (mg/ml): | 0.235 | 0.395$^b$ | 0.267 | 0.237 | 0.256 | −0.161 | 0.285$^a$ |
| MBPLM (ng/ml): | 0.059 | 0.262 | 0.244 | 0.250 | 0.212 | −0.201 | 0.210 |
| MBPLM/Cr. (ng/mg): | −0.077 | −0.063 | 0.093 | 0.163 | 0.107 | −0.160 | 0.070 |

The numbers are the Pearson correlation coefficients. Values with statistically significant differences are shown in bold type and the range of p-values referenced as $^a$p-value <0.05, $^b$p-value <0.01, $^c$p-value <0.005.

better) between the measurements of creatinine, myelin basic protein-like material, myelin basic protein-like material/creatinine, the number of lesions and total lesion area on MRI with the change of relapsing-remitting to

TABLE 2

Correlations Of Urinary Myelin Basic Protein-Like Material Variables With MRI And Clinical Measures

| | MRI | | | | Clinical | | |
|---|---|---|---|---|---|---|---|
| | Percent Activity | New Lesions | Number of Lesions | Total Area | EDSS | Scripps | Change to Prog. |
| Group 2 Overall (N = 802) | | | | | | | |
| Creatinine (mg/ml): | 0.160$^c$ | 0.030 | 0.273$^c$ | 0.249$^c$ | 0.040 | −0.101$^a$ | 0.216$^c$ |
| MBPLM (ng/ml): | 0.034 | −0.034 | 0.248$^c$ | 0.237$^c$ | 0.074$^a$ | −0.112$^a$ | 0.257$^c$ |
| MBPLM/Cr. (ng/mg): | −0.164$^c$ | −0.127$^c$ | 0.082$^a$ | 0.124$^c$ | 0.097$^b$ | −0.110$^a$ | 0.169$^c$ |
| Group 2 Visit 1 (N = 43) | | | | | | | |
| Creatinine (mg/ml): | 0.243 | 0.380$^a$ | 0.267 | 0.258 | 0.304$^a$ | −0.161 | 0.250 |
| MBPLM (ng/ml): | 0.095 | 0.258 | 0.244 | 0.368$^a$ | 0.377$^a$ | −0.201 | 0.172 |
| MBPLM/Cr. (ng/mg): | −0.062 | −0.058 | 0.093 | 0.238 | 0.205 | −0.160 | 0.074 |
| Group 2 Visit 2 (N = 39) | | | | | | | |
| Creatinine (mg/ml): | 0.049 | −0.119 | 0.368$^a$ | 0.384$^a$ | 0.098 | −0.326 | 0.456$^c$ |
| MBPLM (ng/ml): | 0.196 | −0.016 | 0.421$^b$ | 0.402$^a$ | 0.282 | −0.235 | 0.475$^c$ |
| MBPLM/Cr. (ng/mg): | 0.024 | 0.052 | 0.292 | 0.185 | 0.297 | −0.033 | 0.144 |

The numbers are the Pearson correlation coefficients. Values with statistically significant differences are shown in bold type and the range of p-values referenced as $^a$p-value <0.05, $^b$p-value <0.01, $^c$p value <0.005.

EXAMPLE 14

Urinary MBPLM and Change to a Progressive Course

When analyzed for a correlation between urinary myelin basic protein-like material and a change from relapsing-remitting to a chronic progressive course, there was a borderline correlation for Group 1 (p=0.0573) but a highly chronic progressive in disease course (Table 2). Consistent with earlier reports that no correlation between disease activity and urinary myelin basic protein-like material/creatinine existed (23), there was a significant negative correlation or indirect relationship between the value of urinary myelin basic protein-like material/creatinine and the number of relapses (p=0.0159).

The urinary level of myelin basic protein-like material was significantly higher in the relapsing-remitting multiple sclerosis patients who had shifted to a chronic progressive course than those who had retained the relapsing-remitting pattern. This was especially noted in the Group 2 cohort of 52 patients who had urine specimens obtained every six weeks and, thus, a larger number of samples for analysis. Those who became chronic progressive had a value of urinary myelin basic protein-like material of 198.5±60 ng/ml urine compared to a value of 129.0±81 ng/ml urine in the relapsing-remitting patients (p=0.0042). The parallel change in creatinine had the effect of changing the relationship of ng MBPLM/mg creatinine and transition of relapsing-remitting to chronic progressive-multiple sclerosis to only a trend (p=0.0752).

When the data from Group 2 were plotted over the course of the trial, the mean value of myelin basic protein-like material was always higher in the chronic progressive compared to the relapsing-remitting group, with a significant difference by 6 weeks and for 9 of the 18 intervals for urine specimen collection (p<0.05). The mean day of onset of the chronic progressive from the relapsing-remitting phase in Group 1 was 566 days. The median for this change was 394 days, reflecting the length of time in some patients for this change to occur. Specifically, of the 19 relapsing-remitting patients who became chronic progressive, 9 did so within the first year, 4 did so between years one and two, 3 between years two and three, and 3 after the third year. When the combined data of Groups 1 and 2 were analyzed in regard to a temporal relationship of the urinary myelin basic protein-like material value and the transition of disease phases, a precise temporal relationship could not be determined, but it was evident that the elevation in urinary myelin basic protein-like material must have antedated the transition in disease phases by months. Thus, before the transition, the mean value of MBPLM in the chronic progressive group (N=150) was 199.9 ng/ml urine, while after the transition, the mean value was 190.6 ng/ml urine (N=93). In the relapsing-remitting group (N=591), the mean value of MBPLM was 131.2 ng/ml urine.

Because of the impact of the elevated creatinine values, the availability of 24 hour urine collections from Group 3 presented an opportunity to address this question with more optimal urine measures. Subject means of urinary creatinine, myelin basic protein-like material (ng/ml urine or ng/24 h urine collection) or ng MBPLM/mg creatinine values showed no significant differences in regard to the "on" or "off" day of administration of IFNβ-1b. Therefore, the data could be combined and averaged for larger group analysis. The chronic progressive group had higher myelin basic protein-like material/creatinine ratios (p=0.0349) than the relapsing-remitting group, but there were no differences between chronic progressive and relapsing-remitting groups in values of creatinine or myelin basic protein-like material. When the amount of myelin basic protein-like material excreted over 24 hours was analyzed, there was no significant difference (p=0.1775). The trend is in the direction of the chronic progressive having a higher value than the relapsing-remitting group.

EXAMPLE 15

Effect of IFNβ-1b Treatment on Urinary MBPLM

For Group 1, there were trends for differences among the three treatment groups. Overall and at each visit, the high dose IFNβ-1b group had higher values of urinary myelin basic protein-like material than both placebo and low dose IFNβ-1b groups. However, these group differences at the start of the trial approached, but did not reach, a significant level (p=0.0753). Although not statistically significant, these trends implied that in the randomized assignment of patients to the three treatment groups at the outset of the trial, there had been an inadvertent selection of multiple sclerosis patients with higher urinary myelin basic protein-like material values assigned to the high-dose treatment group. For visit 2, the difference reached a significant level overall (p=0.0365), with the urinary myelin basic protein-like material elevated in the high dose group compared to the placebo group (p=0.0204), and the high dose group compared to the low dose treatment group (p=0.0296). This indicated that the differences in urinary myelin basic protein-like material values noted in the 3 treatment groups at the beginning of the trial became more evident by the beginning of the second year of the trial. This difference became insignificant again by the third visit because of an increase of urinary myelin basic protein-like material in the placebo group between visits 1 and 3 (p=0.0056) and between visits 2 and 3 (p=0.0014). Because of the significant differences in urinary myelin basic protein-like material values among the randomly assigned treatment groups, correlation studies for treatment effects were precluded for Group 1. Specifically, there was no definite treatment effect that could be demonstrated on the basis of levels of urinary myelin basic protein-like material.

Group 3 patients, from whom urine was collected in mid-trial, were also analyzed for treatment effect, and creatinine values were not different among the placebo, low dose IFNβ-1b or high dose IFNβ-1b groups. However, the value for myelin basic protein-like material (ng/ml urine) was significantly higher in the placebo group than in either the low dose (p=0.0005) or high dose (p=0.0023) IFNβ-1b groups. Similarly, the values for myelin basic protein-like material/creatinine were significantly higher in the placebo group than in either the low dose (p=0.0003) or high dose (p=0.0014) IFNβ-1b groups. These differences between placebo and low dose (p=0.0001) and placebo and high dose (p=0.0039) groups were also evident when the myelin basic protein-like material measurements were expressed as amount during a cumulative 24 hour urine collection period. Since there were no baseline samples collected for Group 3, these significant differences, as striking as they are, possibly could have arisen from the random assignment to treatment groups.

In a two-factor ANOVA, the treatment and progression variables were studied simultaneously in Group 3. A significant interaction existed between effect on the value of myelin basic protein-like material expressed as a 24 hour collection (p=0.0108) or adjusted for creatinine (p=0.0303). When analyzed further, it was clearly demonstrated that the relapsing-remitting group receiving placebo and which eventually became chronic progressive was the major variable accounting for these differences. By the same analytical methods, there was no significant interaction of these same two variables on the values of creatinine or myelin basic protein-like material (ng/ml). Covariance analyses, performed to account for the effect of the variation in length of time in the clinical trial when the specimens were collected, gave the same results as the ANOVA's. The simpler ANOVA results are therefore presented herein. It was noted that the standard deviations for these measurements in Group 3 were large and proportional to the means. Since the arithmetic means departed from a normal distribution, a logarithmic transformation was applied and the data reanalyzed. The myelin basic protein-like material variable measured over a 24 hour collection period remained significant (p=0.0283), while the myelin basic protein-like material adjusted for creatinine was no longer significant between the treatment and progression variables (p=0.0792).

In another effort to delineate the timing and prediction of a relapsing-remitting and chronic progressive course with any treatment effect, all urine data from Groups 1 and 2 were combined. In doing so, it was first shown that patients in the chronic progressive and relapsing-remitting categories were equally distributed among the three treatment groups (p=0.901). When grouped by any of the treatments versus placebo, there was not a significant treatment effect (p=0.891). The means and slopes of urinary myelin basic protein-like material were computed for all patients. The only significant difference was found in the average level of myelin basic protein-like material (ng/ml) with respect to progression (p=0.0051). There was no significant effect with regard to treatment. In another attempt to detect predictive differences in urinary myelin basic protein-like material values for the relapsing-remitting and chronic progressive groups, means and slopes for relapsing-remitting and chronic progressive groups were computed using values obtained before the transition to chronic progressive from relapsing-remitting. There was a significant difference between the relapsing-remitting and chronic progressive groups in average myelin basic protein-like material (ng/ml) (p=0.0169) and average creatinine (mg/ml) (p=0.0378) before transition. A higher slope in the level of myelin basic protein-like material/creatinine (ng/mg) correlated with a change of relapsing-remitting to chronic progressive course (p=0.0052). There were no significant differences according to treatment.

EXAMPLE 16
Repeat Analysis with Urinary Myelin Basic Protein-Like Material Measured with Antibody R3794 or F41

Three antibody reagents are now available which detect urinary myelin basic protein-like material. These are R110 (22), which has been used to obtain the myelin basic protein-like material values analyzed above, polyclonal reagent R3794 and mAb F41 (35).

All three react with cryptic epitopes in myelin basic protein (22, 35).

The urine samples collected annually (Group 1) were tested in RIAs with F41 and R3794, and the values obtained were compared with those from the measurements with R110. R110 and R3794, which recognize epitopes in myelin basic protein peptide 83–89 and 84–89, respectively, revealed similar correlations for Group 1. Monoclonal antibody F41, which recognizes a different epitope in myelin basic protein (peptide 80–85) demonstrated no difference.

EXAMPLE 17
Childhood and Urinary Myelin Basic Protein-Like Material

The present invention demonstrates that the level of urine myelin basic protein-like material can be utilized successfully as a marker of disease status in adults with multiple sclerosis.

Myelin basic protein-like material increases in patients changing from a relapsing-remitting to a progressive course, possibly reflecting attempted or failed remyelination. Scant information exists concerning the presence of, or specific levels of, urine myelin basic protein-like material during infancy and childhood when myelination is most active. If urine myelin basic protein-like material exhibits a developmental profile corresponding to that of forebrain myelination, certain inferences should follow deviations from normal. Myelin basic protein-like material, as shown herein, can serve as a monitor of neurodevelopmental status in infants at risk for adverse outcomes.

The present invention demonstrates the pattern of myelin basic protein-like material in normal children ranging in age from birth (at full term) to age 17 years. Urinary myelin basic protein-like material was assayed as described above from 398 infants and children. The group consisted of 257 males (65%). These children had no known neurological or neurodevelopmental abnormality. Children with acute infections (urinary tract or upper respiratory tract) or chronic disease (diabetes, renal or collagen-vascular) were excluded. All children were cleared by the attending (in the case of newborns) or primary physicians and by the UAB Institutional Review Board. All samples were obtained by voiding into an external collection bag or urine specimen container.

The level of urinary MBPLM was determined by the above-described double antibody radioimmunoassay. Radiolabeled human MBP peptide residues 69–89 served as the radioligand and rabbit 110 (R110) antiserum as the first antibody. MBP peptide residues 83–89 was the inhibitor standard. For relating MBPLM values to renal function, urinay creatinine was measured using a kit assay, and the level of MBPLM (ng) was expressed relative to the level of creatinine (mg).

Urinary levels of MBPLM, expressed as ng/mg creatinine or as ng/ml urine, were grouped according to age and gender. Means, standard deviations and standard errors were computed for each group. As the population sample was cross-sectional, the groups included newborns and one year increments thereafter. Means for each age group were compared to the adult control group mean using Dunnert's T-test. Results were considered significant at a p value of <0.05.

Revalidation of the urinary MBPLM assay in the age group of 1 month-5 years revealed no significant differences from the (within) assay variance of 11.3%, the (between) assay variance of 12.4%, and the 80–94% recovery of peptide residues 83–89. These results excluded the possibility of age-related effects on the validity of the assay which might affect the measurements recorded. Furthermore, urinary creatinine values from the cohort in the study were analyzed with regard to age. Creatinine was lower (0.04–0.10 mg/ml) from newborn through 3 years and higher (1.74–2.36 mg/ml) in the ages of 14–17 years. The difference from control values is significant for both age groups, indicating that the values for MBPLM/creatinine (ng/mg) overstate the amount of urinary MBPLM excreted in the youngest groups and understate it in the older group. Additionally, due to a refinement in the method of creatinine measurement, adult control values were recalculated to a mean creatinine level of 1.05 mg/ml, resulting in an adult control value for MBPLM of 157.3±83.9 ng/ml creatinine (FIG. 1).

EXAMPLE 18
Age-Related Changes in the Level of Urinary Myelin Basic Protein-Like Material During Childhood Myelin basic protein-like material was detectable in urine from newborns, although at substantially lower levels than in adults. Whether expressed as ng/ml urine or ng/mg creatinine, myelin basic protein-like material levels were low from birth though 12 months, then increased linearly through age 5, exceeding established control values for adults by more than 2-fold. Thereafter, myelin basic protein-like material levels decline to adult levels by age 10–13. Human urine myelin basic protein-like material exhibits a developmental profile that parallels the onset of normal myelination, actually exceeding normal values through early childhood. Thus, urinary myelin basic protein-like material can serve as a useful marker for normal or aberrant myelination in the developing child.

FIG. 1 shows the age-related changes in urinary MBPLM expressed as ng/mg creatinine, however, it should be emphasized that whether expressed an ng/ml urine or ng/mg creatinine, the pattern of MBPLM in urine relative to age groups was virtually identical. Urinary MBPLM levels, expressed as either ng/ml urine, or ng/mg creatinine, were <10% of adult values from birth through age 1 year. Thereafter, MBPLM values increased rapidly, exceeding the adult range by age 3 years. Whether expressed as ng/mg creatinine or ng/ml urine, urinary MBPLM achieves maximal values at ages 5–6 years of age (348.0±254.6 ng/mg creatinine), declining thereafter to adult values around age 13 years. In spite of the wide range of values, urinary MBPLM in newborns (35.9±85.6 ng/mg creatinine) was significantly lower ($p<0.05$) than in normal adults. From ages 2–3 years through 7–8 years, urinary MBPLM expressed as ng/mg creatinine was significantly higher. Urinary creatinine is about 20% lower in females than males. Analysis on a gender basis revealed both males and females had significantly lower urinary MBPLM (ng/mg creatinine) as neonates compared to adult control values. At ages 2–3 and 6–7 years in females and at ages 5–6 and 7–8 in males, urinary MBPLM (ng/mg creatinine) was significantly higher ($p<0.05$) than adult values.

The key neurodevelopmental events occurring in the cerebral hemispheres during the postnatal period encompassed herein relate to dendritic development, synaptogenesis in gray matter and myelination in white matter. Most neuronal proliferation and migration in the cerebrum has concluded by the end of the second trimester, however, dendrites proliferate dramatically during the last trimester through the first birthday. Myelination in the human forebrain also begins well after neuronal proliferation and migration have been virtually completed and continues actively through much of the first decade. Volumetric MRI studies indicate that much of the postnatal increase in brain volume is attributable to the white matter compartment and, by inference, to mylinogenesis.

The temporal pattern of urinary MBPLM expression mirrors that established for myelination in the central nervous system. The human forebrain is myelinated by 24 months of age, although active myelination appears to continue into early adulthood. Children with impairments in normal myelination, or with neurodegeneration (inherited or acquired) leading to de- or dys-myelination, are examined using the methods described herein. Recent data clearly demonstrates abnormal myelination in the 18q-syndrome, which, among others, affects the gene for MBP. It would be predicted that children with 18q syndrome, as well as the mouse analogue, the shiverer mouse, would be deficient in MBP synthesis, and thereby excrete less urinary MBPLM. Furthermore, the ever-expanding group of preterm births, beginning at 23–24 weeks gestation, well before the onset of central myelination, is an important population in which to examine urinary MBPLM.

EXAMPLE 19
Changes in the Level of Urinary Myelin Basic Protein-Like Material

The present invention demonstrates that the level of urinary myelin basic protein-like material correlates with, or is a predictor of, the transition of multiple sclerosis from relapsing-remitting phase to chronic progressive phase. The elevated level of urinary myelin basic protein-like material occurred well in advance of the clinical designation of a chronic progressive course, indicating that the level of urinary myelin basic protein-like material may be important in stratifying multiple sclerosis patients prior to entering a clinical trial. The exact level of urinary myelin basic protein-like material which signals a progressive course must be examined closely because of the fluctuations over time in the same patient.

Because the conditions and collection of urine specimens were obtained from a clinical trial not specifically designed to address a change in urinary myelin basic protein-like material levels, the results revealed the imperfections as to how the urine was sampled and how the myelin basic protein-like material measurements were made. The greatest challenge to the use of urinary myelin basic protein-like material as a surrogate marker is the effect of urinary levels of creatinine. For reasons that are currently unclear, patients with chronic progressive-multiple sclerosis also had higher levels of creatinine. Such a change in creatinine concordant with that of myelin basic protein-like material diminished the predictive use in Group 1 of myelin basic protein-like material/creatinine, the ratio shown to be the most desirable to normalize for glomerular function (22, 23). The effect of creatinine was most noted in Group 2. It was in Group 2 that the level of myelin basic protein-like material alone or myelin basic protein-like material/creatinine was significantly higher in the chronic progressive cases. Furthermore, the slope in myelin basic protein-like material/creatinine in Group 2 and the 24 hour collections in Group 3 also showed a correlation of urinary myelin basic protein-like material and chronic progressive disease course.

The IFNβ-1b trial was completed before it became clear that urinary myelin basic protein-like material was not directly correlated with acute clinical disease activity (23), as is CSF myelin basic protein-like material (19, 36). Specifically, levels of urinary myelin basic protein-like material/creatinine do not correlate with clinical relapse, gadolinium enhancement of lesions detected on cranial MRI or level of myelin basic protein-like material in CSF (23). In the present invention, urinary myelin basic protein-like material did not correlate with the number of clinical relapses. However, urinary myelin basic protein-like material levels did correlate overall with the number of lesions and total lesion burden as determined by T2-weighted cranial MRI.

Since a beneficial effect of IFNβ-1b was demonstrated in the clinical trial (24), a correlation or prediction of treatment effect was sought. The level of urinary myelin basic protein-like material rose more in the placebo group than in either of the IFNβ-1b treatment groups, and in Group 3 it was clearly the placebo-treated patients undergoing a transition to the chronic progressive phase who had the highest levels of urinary myelin basic protein-like material. However, the trial in which patients were randomly assigned to placebo, low-dose IFNβ-1b or high-dose IFNβ-1b did not control for urinary myelin basic protein-like material upon entry.

The mechanism for a rise in the level of urinary myelin basic protein-like material is not yet known. The information available indicates that large myelin basic protein peptides are likely to be rapidly cleared (37) and degraded (38) in the kidney. Since the immunochemical form of myelin basic protein-like material in the urine is different from that in the CSF (22), and since the levels of myelin basic protein-like material in CSF and urine are not directly related (23), the mechanism for the rise of myelin basic protein-like material in CSF, presumably acute myelin or oligodendrocyte damage, is unlikely to be the same as that in the urine. Axonal contact upregulates the synthesis of myelin basic protein synthesis by oligodendrocytes in the absence of axons (39). Thus, oligodendrocytes in the demyelinated and chronic lesions of multiple sclerosis may continue to synthesize myelin basic protein in the chronic progressive course of multiple sclerosis when axonal loss is presumed to occur. Synthesized myelin basic protein, which is not incorporated into myelin precursors or into myelin itself, may reach the circulation and be cleared and degraded by the kidney. The small, cryptic epitope of myelin basic protein would thereby enter urine and be detectable in the immunoassay.

The present invention represents a first approximation of the correlation and prediction of the level of myelin basic protein-like material in urine and other body fluids and the future disease course of multiple sclerosis. The immunochemical detection of MBPLM as a cryptic epitope in the carboxyl portion of myelin basic protein peptide 80–89 (40) and confirmation of the measurements with a second antibody (with a nearly identical epitope recognition domain (35)) add to the validity of the immunoassay. The relationship of urinary myelin basic protein-like material with chronic progressive disease, more precise classification of disability status, clarification of the differences of the subtypes of multiple sclerosis (especially relapsing-progressive and relapsing-remitting) and the delineation of the type of cranial MRI technique to be utilized makes the outcomes of future clinical trials in multiple sclerosis more accurate and their conduct more rapid.

EXAMPLE 20

Reagents and Equipment for Determination of the p-Cresol Sulfate Component in MBPLM Sequenal grade trifluoroacetic acid (TFA), heptafluorobutyric acid (HFBA), triethylammonium acetate (TEA), triethylammonium phosphate (TEAP) and acetonitrile (ACN) were purchased from Pierce Chemical Company (Rockford, Ill.). The deionized and organic-free water (dIH$_2$O) for making HPLC solution was obtained by applying "Milli-Q" Water System from Millipore (Milford, Mass.). High performance liquid chromatography (HPLC) was performed on a Waters liquid chromatography system equipped with a model 590 pump, model 510 pump, WISP model 712 autosampler, and a model 450 ultraviolet absorbance detector. Data were acquired and processed with Waters Expert chromatography software from Millipore Corporation, which was operated in a computer Digital 380 from Digital Equipment Corporation (Maynard, Mass.). The Waters Sep-pak Plus cartridges (Millipore, Milford, Mass.) for solid phase extraction of urine MBPLM were as follows: tC$_{18}$ for reverse-phase extraction, Accell QMA for anion exchange and Accell CM for cation exchange extraction. Human MBP peptides 68–72, 80– 89, 81–87, 82–89 and 83–89 were synthesized by Peninsula Laboratories (Richmond Calif.). p-Cresol, m-cresol and o-cresol were commercially obtained (Aldrich, Milwaukee Wis.).

EXAMPLE 21

Quantitation of MBPLM

An equilibrium double antibody radioimmunoassay (DA-RIA) (22, 23) was used to quantitate the level of MBPLM in urine samples and to monitor the isolation of MBPLM during the different fractionation procedures. The primary antiserum, R110, was used at a final dilution of 1:1750. The $^{125}$I-labeled antigen was human MBP peptide 68–89. Based on the epitope recognized in MBP by R110 serum (22) and the parallelism by RIA (47), human MBP peptide 83–89 was used as the RIA standard. This RIA was also used to measure the reactivity of isomers of cresol and cresol sulfate. A second RIA was used for the detection of MBPLM in cerebrospinal fluid (CSF) (49). The RIA used for MBPLM in CSF detects a noncryptic epitope in MBP peptide 80–89 and does not detect MBPLM in urine (22).

EXAMPLE 22

Patient Specimens and Preliminary Processing of Urine

Urine specimens were obtained from two clinically definite MS patients and one volunteer. This study was approved by the Institutional Review Board. Patient One was a 47 year-old female with RR-MS for 14 years (46). Urine was collected during a period of remission and stabilization, at which time the patient's Expanded Disability Status Scale (EDSS) (25) score was 2.5. Patient two was a 47 year-old male with SP-MS who had had a RR course for 9 years, but had shown progression for 5 years. Urine was collected during a period of gradual progression when his EDSS was 6.5 and over a year after his last clinical relapse. Neither patient had been treated with glucocorticoids for over one year and neither had ever been treated with chemotherapeutic or immunomodulatory agents. Specimens were frozen at −20° C. until use. Urine samples from these two MS patients were not mixed during the purification steps.

Figure 2:
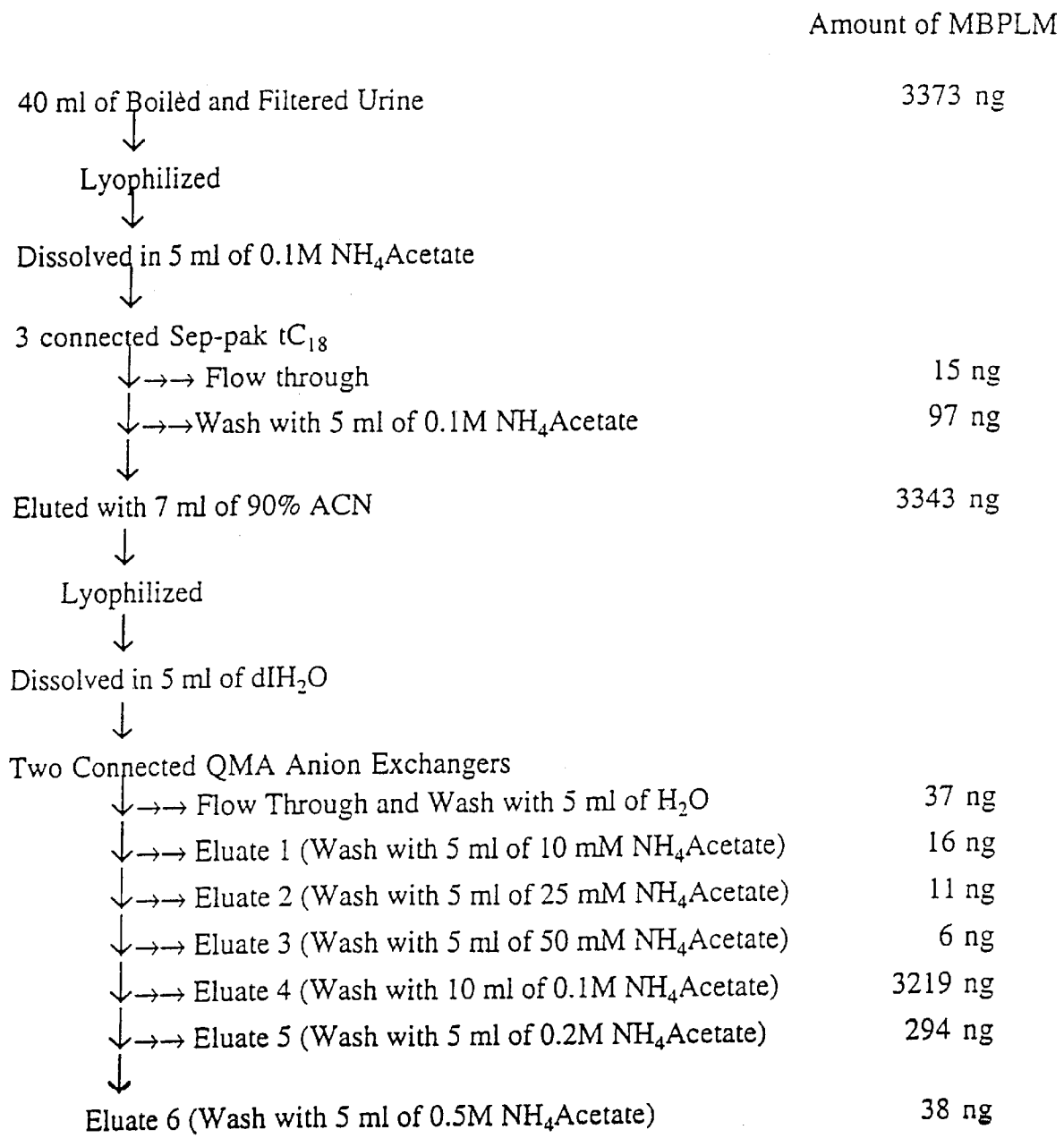
FIG. 2 shows the initial processing of urine with reverse phase followed by anion-exchange extraction. Urine was boiled for 10 min, passed through a 0.22 μM filter, and after lyophilization, passed through reverse phase $tC_{18}$ Sep-pak and, then through an anion-exchange Sep-pak with a yield of over 95%.

Urine was thawed at 25° C., boiled for 10 min, allowed to cool to 25° C., filtered through a 0.22 µm membrane, dried by lyophilization, and reconstituted in 0.1 M ammonium acetate in a volume 10% of the starting volume of the urine. A two-step extraction of MBPLM was then performed on tC$_{28}$ cartridges for reverse phase extraction and on Accell QMA for anion exchange extraction (FIG. 2).

EXAMPLE 23

High Performance Size Exclusion Chromatography (HPSEC), Reverse Phase HPLC (RP-HPLC) and High Performance Anion Exchange Chromatography (HPAEC)

The Sep-pak extract of urine was further purified on a HPSEC column SEC2000 (Beckman, Fullerton, Calif.) which has a range of separation over a molecular weight of 1–250 kDa. The sample was dissolved in 0.2 M ammonium acetate (pH 6.0) or 0.1% acetic acid and eluted isocratically. The eluted fractions containing MBPLM were identified by RIA and applied to reverse phase HPLC (RP-HPLC). A HPSEC column (Waters Shodex OHpak Q-801/S) for separation of molecules smaller than 1000 Da with a mobile phase of either 0.1 M ammonium hydroxide or 0.1% acetic acid, was used for final purification steps just prior to structure analysis.

C$_4$, C$_{18}$, phenyl and polymer (Vydac 259VHP54) columns were obtained from Vydac (Hisperia, Calif.). The SEC2000 column (Beckman, Fullerton, Calif.) fractions with MBPLM were further purified by a combination RP-HPLC steps using a C$_4$ followed by a C$_{18}$ column for which the aqueous phase was 0.115% TEA (pH 5.0), and the organic modifier used was ACN. The optional aqueous phase was 0.1% TFA or TEAP. Using a Protein Pack column DEAE 5PW (Waters, Milford, Mass.), fractions containing MBPLM were eluted from the column with a gradient from dIH$_2$O to 0.2 M ammonium acetate.

EXAMPLE 24

Affinity Chromatography and Peptide Analysis

Two monoclonal antibodies (mAbs), 845D3 directed towards human MBP peptide 80–89 (50), and mAb F41B5 directed against human urine with a high MBPLM level and reactive with MBP peptide 80–85 (35), were purified by immunoaffinity chromatography using immobilized human MBP peptide 45–89 (45). The purified mAb was coupled to activated Sepharose CH 4B gel (Pharmacia. Uppsala, Sweden) for soft gel immunoaffinity extraction of urinary MBPLM from urine. The urine sample, which had been boiled and filtered, was slowly passed through the column and followed by elution with 0.1 M ammonium acetate (pH 3.5).

For high performance immunoaffinity chromatography, 26 mg of mAb 845D3 was coupled to an ULTRAFFINITY-EP column (Beckman, Fullerton, Calif.) using a procedure recommended by the manufacturer. The patient urine fraction, dissolved in phosphate buffered NaCl (PBS) (pH 6.5), was pumped through the column and washed with sample buffer. 0.1% TFA (pH 2.4) containing 20% ACN was used as an eluant. The material was eluted rapidly, and after desalting and concentration, was processed by RP-HPLC.

For immunoaffinity extraction of urinary MBPLM on Acti-disk (Whatman, Clifton N.J.), 45 ml of urine was reacted with 2 mg of affinity purified mAb 845D3 or mAb F41C11 for 24 hours at 4° C. prior to exposure to and recovery from the Acti-disk to which protein-G was attached. The antibody and captured molecules were eluted with 0.5 M ammonium acetate (pH 3.0), and separated from each other by Amicon centri-prep 10 (Beverly, Mass.) to remove the antibody prior to RP-HPLC. Amino acid analysis was performed with the Picotag system (Waters) and samples were additionally processed for amino-terminal sequencing by the Edman method.

EXAMPLE 25
Mass Spectrometry and Nuclear Magnetic Resonance

Analyses were performed on an API III triple quadrupole mass spectrometer (PE-Sciex, Concorde, Canada) by either the flow injection methods or by RP-HPLC mass spectrometry (MS) using electrospray MS (ESMS) in the negative mode. For flow injection, the samples in a solution of 50/50 ($dIH_2O$/ACN) containing 0.1% formic acid were injected into a 25 $\mu$l/ml flow of the same solvent system delivered by a Harvard Apparatus model 22 syringe pump to the ESMS interface. For RP-HPLC MS, HPLC analyses were performed using a 4.6×100 mm Aquacare C8 RP-HPLC column employing a gradient of 0–100% ACN in 0.1% formic acid over 12 min at a flow rate of 1 ml/min. Analyses using isocratic conditions (20% ACN in 0.1% formic acid) were used for multiple reaction monitoring (MRM). In either gradient or isocratic runs, the flow of 1 ml/min from the RP-HPLC was split to deliver approximately 40 $\mu$l/min to the ESMS. Tandem MS (MS/MS) daughter ion spectra were obtained by passing the (M−H)⁻ ion selected with the first quadrupole into the second quadrupole containing argon gas and analyzing the fragment ions with the third quadrupole. MRM was conducted in a manner similar to MS/MS by selection of specific ions not only in the first quadrupole, but also in the third quadrupole. Integration of peak areas was performed with the program McQuan provided by the manufacturer of the MS. The areas were compared to the areas of a set of known standards in order to estimate concentrations.

NMR experiments were recorded on a Bruker DRX400 spectrometer operating with a 5 mm inverse-detect probe. Samples were dissolved in dimethylsulfoxide-d6 (Aldrich), and their molarity was expressed as mass/volume using a mass of 187 for cresol sulfate. Sample concentrations were p-cresol sulfate (2.0 mM), MBPLM (2.0 mM), o-cresol sulfate (3.2 mM) and m-cresol sulfate (10 mM). $^1H$ spectra were acquired with a spectral width of 8012.8 Hz and a relaxation delay of 3.0 seconds. The numbers of scans acquired was varied according to the sample concentration. $^{13}C$ spectra were acquired at 100.625 MHz field strength with a spectral width of 31847 Hz, and a 30 degree pulse angle. All spectra were processed using an exponential window function. Spectra were referenced to internal 3-(trimethylsilyl)-1-propane-sulfonic acid, sodium salt (Aldrich).

EXAMPLE 26
Removal of Sulfate-Containing Groups and Preparation of Sulfated p-Cresol Purified MBPLM was treated with sulfatase (51) or subjected to solvolysis (52) with $H_2SO_4$. p-Cresol sulfate, m-cresol sulfate, o-cresol sulfate, and p-cresol sulfonate were synthesized (48). The isomers of cresol sulfate were purified by a combination of chromatography including $tC_{18}$ extraction, HPLC on a Vydac $C_{18}$ column with TEA, and HPSEC on a Waters Shodex Q801/S column with 0.1 M $NH_4OH$. These steps were identical to those used for isolation of urinary MBPLM. The purified samples were lyophilized and subjected to immunological characterization by RIA and chemical characterization by MS and NMR spectroscopy.

EXAMPLE 27
Initial Processing of Urine

After preliminary steps of heating and filtration, a two-step extraction of MBPLM was performed on $tC_{18}$ cartridges for reverse phase extraction and on Accell QMA for anion exchange extraction (FIG. 2). A solution of urine, reduced 10-fold in 5 ml of 0.1 M ammonium acetate, was loaded onto a series of three-connected $tC_{18}$ cartridges and washed with 5 ml of 0.1 M ammonium acetate. The retained materials were eluted with 90% acetonitrile in the same sample buffer. The eluate, containing over 90% of the MBPLM in the starting urine sample, was dried down by vacuum evaporation with a Speed Vac Concentrator (Savant Corp., Farmingdale N.Y.) and dissolved in 5 ml of deionized water ($dIH_2O$). This step was very effective in desalting and is required for successful purification by ion exchange extraction. The advantage of using 0.1 M ammonium acetate as sample and washing buffer is that its higher ionic strength enhances the interaction between peptide and column. Most of the salt in the urine was washed out by ammonium acetate, which is subsequently removed in the volatile phase under vacuum. The $tC_{18}$ extract of MBPLM, dissolved in 5 ml of $dIH_2O$, was loaded onto two serially connected cartridges of Waters Accell QMA anion exchange. Elution was in steps using $dIH_2O$ followed by ammonium acetate in concentrations of 10 mM, 25 mM, 50 mM, 100 mM and 200 mM in a volume of 5 ml each. The MBPLM was eluted by 100 mM ammonium acetate (FIG. 2). Many impurities were removed by this step, in that after the MBPLM was eluted, heavily pigmented contaminants from the applied sample remained on the column even after washing with 0.5 M ammonium acetate alone or with 50% ACN. Removing the pigmented, adherent materials prevented such materials from being irreversibly absorbed by HPLC columns and impeding fractionation. On the basis of monitoring MBPLM content by RIA (FIG. 2), the yield was approximately 60% (Table 3).

TABLE 3

Isolation of Urinary MBPLM for Chemical Characterization

| Steps | Volume (ml) | Concentration (ng/ml) | Total (ng) | Yield (%) |
| --- | --- | --- | --- | --- |
| Urine | 50 | 57 | 2850 | 100 |
| YC-05 filtration | 45 | 58 | 2651 | 93 |
| $tC_{18}$ extraction | 7 | 307 | 2150 | 75 |
| Anion exchange extraction | 5 | 328 | 1640 | 58 |
| HPSEC on SEC2000 | 5 | 226 | 1130 | 40 |

TABLE 3-continued

Isolation of Urinary MBPLM for Chemical Characterization

| Steps | Volume (ml) | Concentration (ng/ml) | Total (ng) | Yield (%) |
|---|---|---|---|---|
| RP-HPLC on Vydac $C_4$ | 7 | 121 | 850 | 30 |
| RP-HPLC on Vydac $C_{18}$ | 4 | 125 | 500 | 18 |
| HPSEC on Waters Q801 | 2 | 200 | 400 | 14 |
| RP-HPLC on Vydac Polymer | 1.5 | 200 | 300 | 11 |

EXAMPLE 28
HPSEC on Beckman SEC2000 Column

Figure 3:
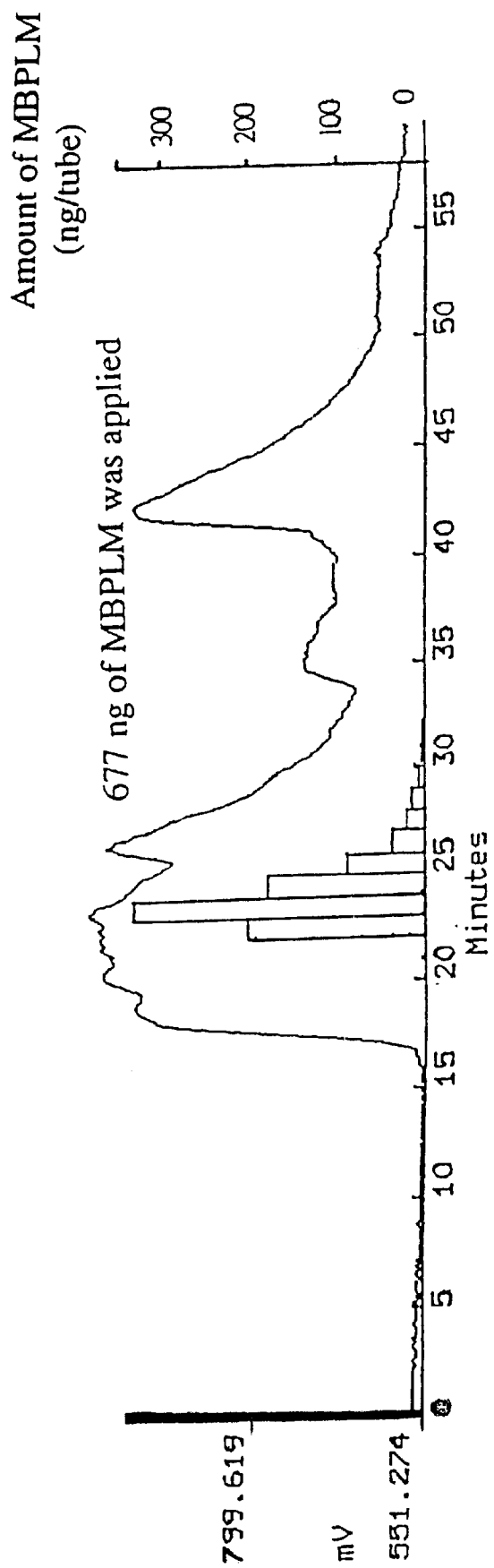
FIG. 3 shows the separation of Sep-pak processed (see FIG. 2) urinary MBPLM (677 ng) by HPSEC (Beckman SEC2000 column 7.5×2300 mm) in 0.2 M ammonium acetate (pH 6.77), at 25° C. RIA monitoring of column eluants revealed that MBPLM eluted within the first major peak at 22–25 min.

The fraction containing MBPLM from QMA anion exchange extraction was lyophilized and reconstituted in 0.2 ml of 0.2 mM ammonium acetate (pH 6.0). The sample was injected onto a HPSEC column (Beckman SEC2000), and sample buffer was used to elute the column at a flow rate of 0.7 ml/min into fractions of 1 min/tube. Under these conditions, MBPLM had a retention time of 23–25 min (FIG. 3) and could be recovered with a yield of over 90% (Table 3). Many urinary constituents different in size from MBPLM were removed by this step. As an alternative, elution with 0.1% acetic acid could also be used for HPSEC on this column without loss of immunoreactivity.

EXAMPLE 29
RP-HPLC on $C_4$ Column with TEA as the Ion Pair

Figure 4:
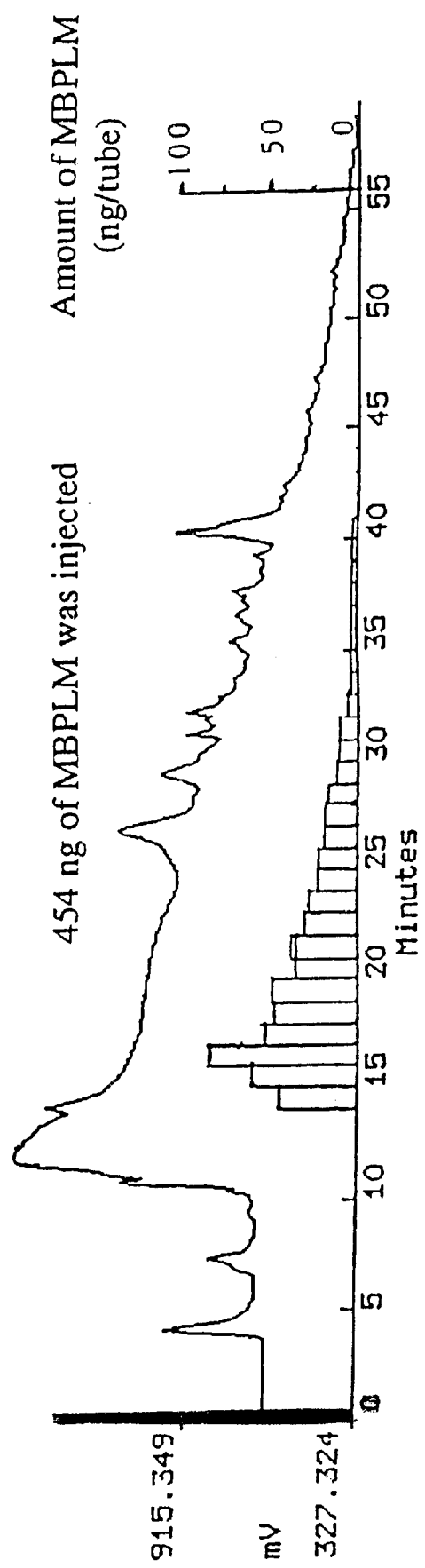
FIG. 4 shows that the urine MBPLM (454 ng) purified by HPSEC (see FIG. 3) was purified further by RP-HPLC (Vydac $C_4$ column, 4.6×240 mm) using buffer A (0.14% acetic acid titrated with TEA to pH 6.69) and buffer B (90% ACN in 0.1% buffer A). The gradient was 0–40% buffer B from 15 to 55 min. Urinary MBPLM eluted as a broad peak between 13 and greater than 25 min and was pooled for further purification.

For further chromatography, the $C_4$ column was used with Buffer A (0.115% acetic acid titrated with TEA (pH 6.0)) and Buffer (90% ACN in Buffer A). The fractions of SEC2000 column which contained MBPLM were dried down and reconstituted in 0.2 ml of Buffer A and loaded on the column. At a flow rate of 1 ml/min, a linear gradient of 0–50% Buffer B was introduced from 15–55 min. The MBPLM eluted as a broad band with a retention time of about 13–20 min (FIG. 4). The fractions containing MBPLM were pooled and dried down.

EXAMPLE 30
RP-HPLC on $C_{18}$ Column with TEA as the Ion Pair

Figure 5:
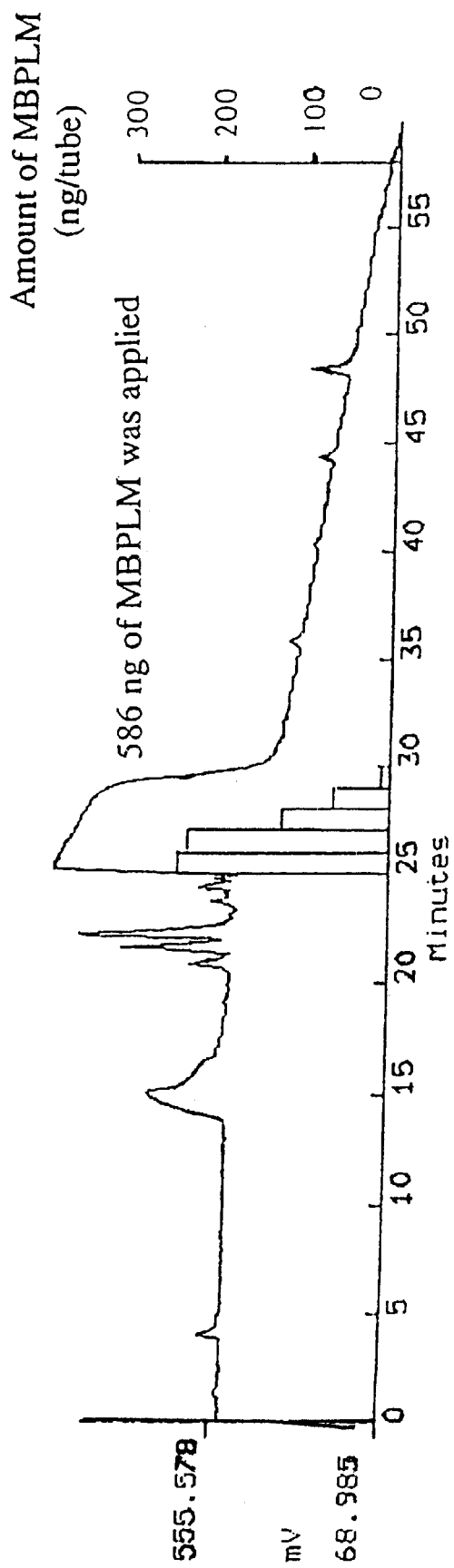
FIG. 5 shows the separation of 586 ng MBPLM fraction from $C_4$ RP-HPLC (see FIG. 4) by RP-HPLC (Vydac $C_{18}$ column, 4.6×240 mm). Buffer A consisted of 0.13% acetic acid titrated with TEA to pH 6.06, and buffer B was 90% ACN in buffer A. The gradient was 0–50% buffer B from 5 to 55 min. MBPLM eluted at 24–29 min.

The next step of purification was on a $C_{18}$ column with the buffers and flow rate identical to those just described for the $C_4$ column, except for the introduction of the gradient of 0–50% Buffer B from 5–55 min. The MBPLM was eluted at 24–28 min (FIG. 5) with a sharper peak than on the $C_4$ column (FIG. 4). Although the fact that the UV absorbance of MBPLM correlated closely with its immunoreactivity implied that a high level of purity of MBPLM had been accomplished, results of its analysis by ESMS and MS/MS could not be interpreted due to the presence of a large amount of TEA from the buffer remaining in the sample, even after several cycles of lyophilization. It was inferred that this retention of TEA was due to its association with the negatively charged groups remaining in the sample and thereby resulting in suppression of the signals on MS of the MBPLM.

EXAMPLE 31
HPSEC on Waters Shodex Q801/S Column with $NH_4OH$

Figure 6:
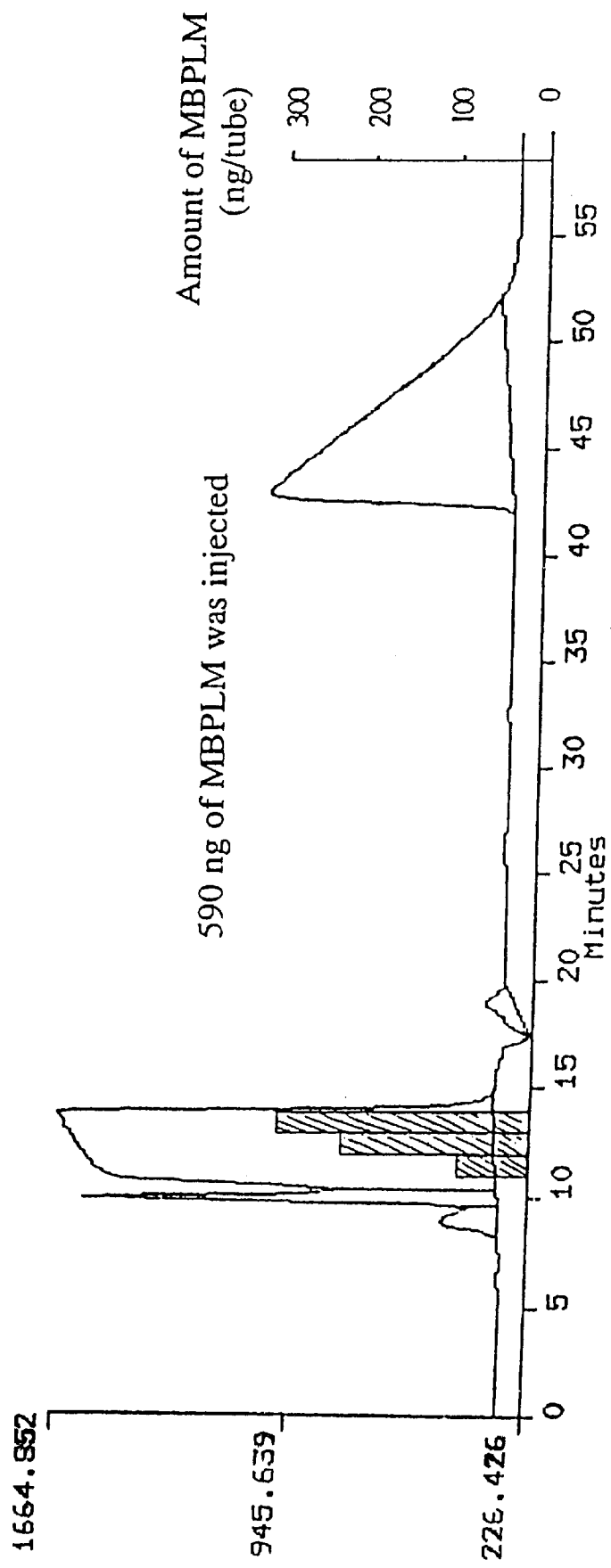
FIG. 6 shows the separation of 590 ng of MBPLM from RP-HPLC $C_{18}$ column by HPSEC (Waters Shodex Q801/S column, 8×250 mm) in 0.1 M $NH_4OH$. MBPLM eluted at 10–13 minutes with TEA eluting after more than 40 min. The UV detection at $A_{215}$ is expressed as $\mu V$.

This step was selected to remove TEA from the sample. The mobile phase was 0.1 M $NH_4OH$ (pH 11.0). This HPSEC column, made of polymer matrix capable of separating molecules over a size range of 100–1000 Da, can withstand the exposure to a high pH. The MBPLM-containing fractions from the $C_{18}$ column were lyophilized and reconstituted in 0.2 ml of 0.1 M $NH_4OH$. After loading the sample, the column was isocratically eluted with the sample solution at 0.5 ml/min at a temperature of 53° C. The MBPLM eluted at 11–14 min, and TEA, which was replaced by the more volatile $NH_4^+$ ion, eluted after more than 40 min (FIG. 6). Column fractions containing purified MBPLM were pooled, and analysis by ESMS was attempted. Certain sulfated compounds co-purified with the MBPLM, and interfered or suppressed signals detected by ESMS.

EXAMPLE 32
HPSEC on Waters Shodex Q801/S Column with Acetic Acid

Figure 7:
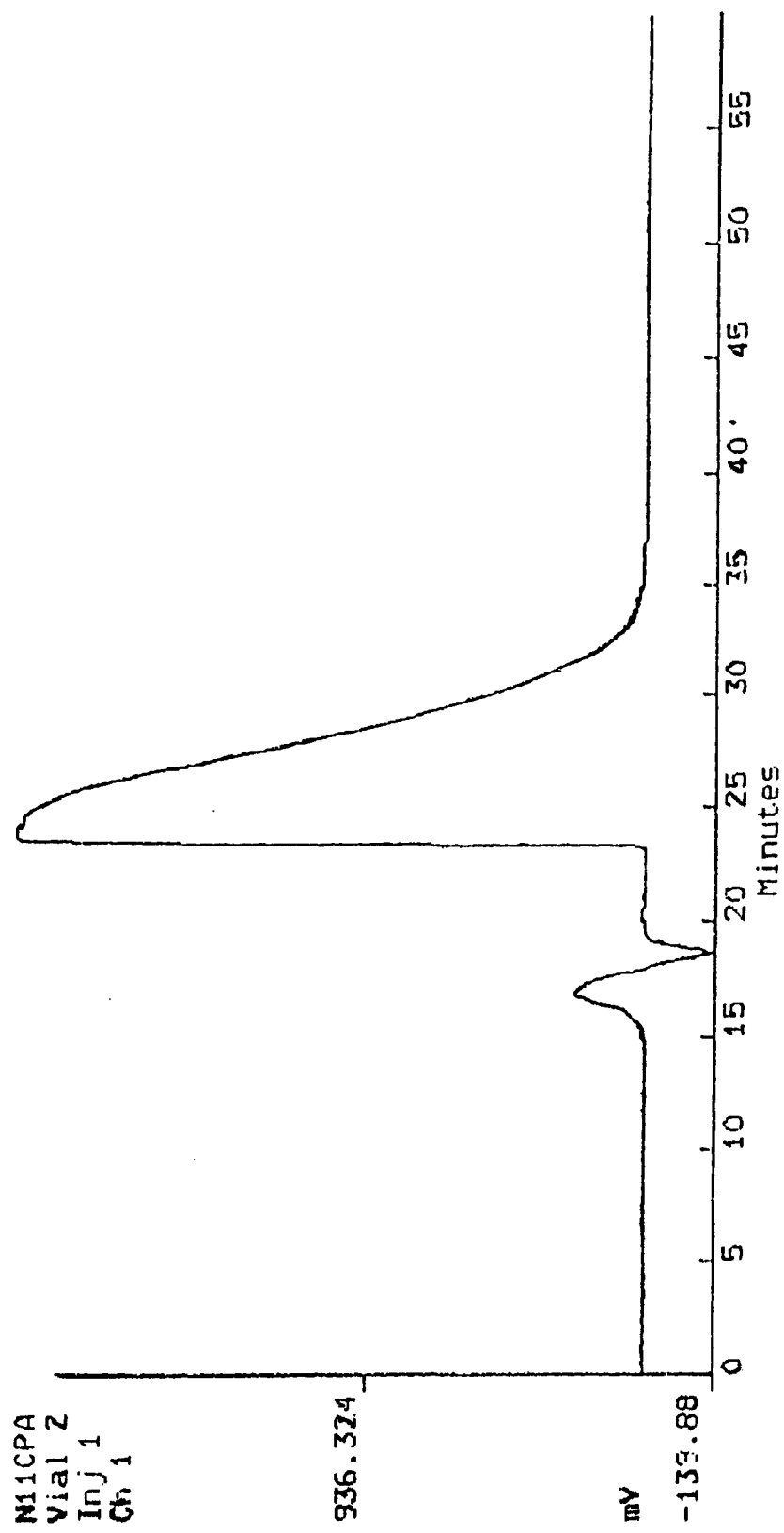
FIG. 7 shows the separation of 205 ng of MBPLM from HPSEC separation by repeat HPSEC (Waters Shodex Q801/S column, 8×250 mm) in 0.1% acetic acid. Using the RIA for monitoring column fractions for content of MBPLM, no immunoreactivity was detected in the peaks detected by UV monitoring at $A_{215}$. Each fraction had a volume of 500 $\mu l$.
Figure 8:
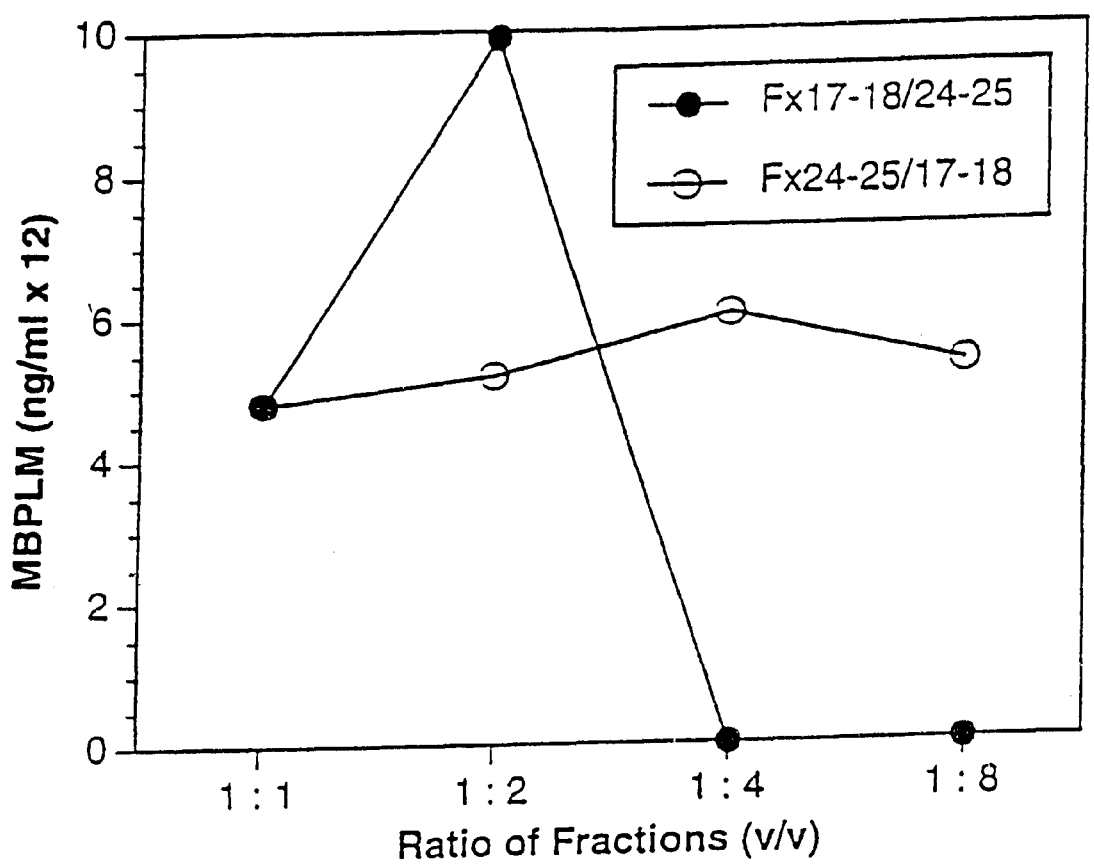
FIG. 8 shows admixture of column fractions recovered from HPSEC in 0.1% acetic acid of MBPLM (see FIG. 7). All individual fractions were negative for MBPLM in RIA. By combining the first peak (i.e., fractions 17–18) and the second peak (i.e., fractions 24–25) obtained by HPSEC, immunoreactive MBPLM could be recovered with maximum reactivity noted when the ratio of the first peak to the second was 1:2.

This step was introduced to more completely remove the salt which interfered with ESMS. Acetic acid was selected because it could be readily lyophilized. The MBPLM purified by HPSEC using the Shodex Q801/S column and $NH_4OH$ (FIG. 6) was dissolved in 0.1% acetic acid and fractionated according to the same conditions (see legend to FIG. 6), except that 0.1% acetic acid, rather than 0.1 M $NH_4OH$, was used as the mobile phase. Under these conditions, the elution profile consisted of two peaks, one at 17–18 min and the other at 23–25 min (FIG. 7). No MBPLM immunoreactivity could be detected in either peak. Given the possibility that MBPLM had been separated into two or more components, each with little or no immunoreactivity by itself, mixing experiments were conducted. Column fractions of 17–18 and 24–25 were mixed at ratios of 1:1 to 1:8 using 25 μl aliquots of each to achieve the ratios. When the peaks were mixed together, over a narrow range and maximally at a ratio of 1 part fractions 17–18 and 2 parts fractions 24–25, the immunoreactivity was restored with recovery of up to 90% (FIG. 8). It was concluded that fractions 24–25 contained the main component for immunoreactivity that was not affected by a ratio of less than 1:1 with fractions 17–18. Both peaks were collected separately and analyzed by mass spectrometry. Masses in fractions 17–18 could not be identified, but there was a sulfate-containing material in fractions 24–25.

EXAMPLE 33
RP-HPLC on Polymer Column

Figure 9:
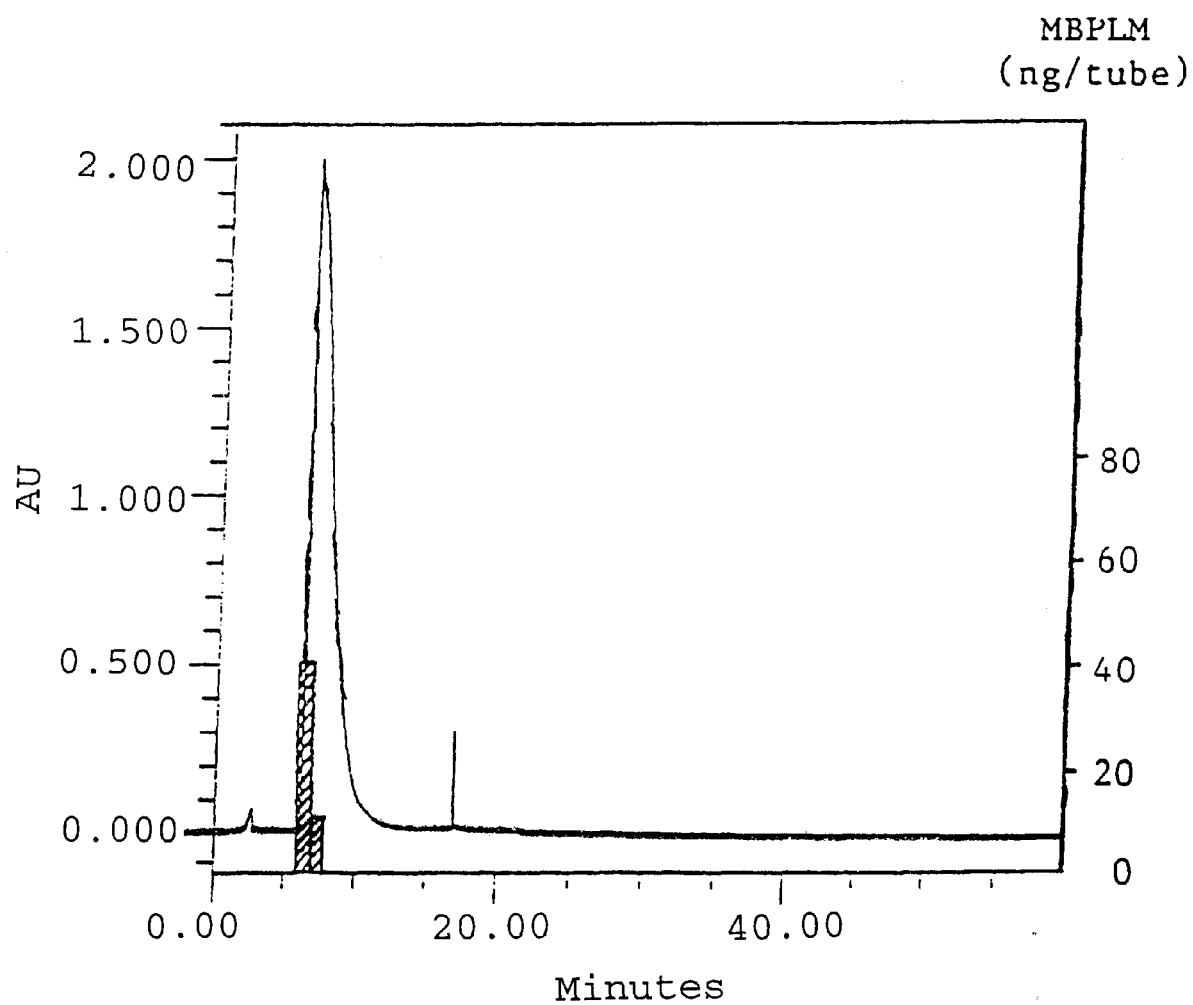
FIG. 9 shows the fractionation of 55 ng urinary MBPLM from HPSEC separation, detected at $A_{215}$ and by RIA, in 0.1 M $NH_4OH$ by RP-HPLC (Vydac Polymer 259VHP54 column. 4.6×25 mm) in 0.1 M $NH_4OH$. The only MBPLM detected by RIA was a single major peak eluting at 7–8 min.
Figure 10:
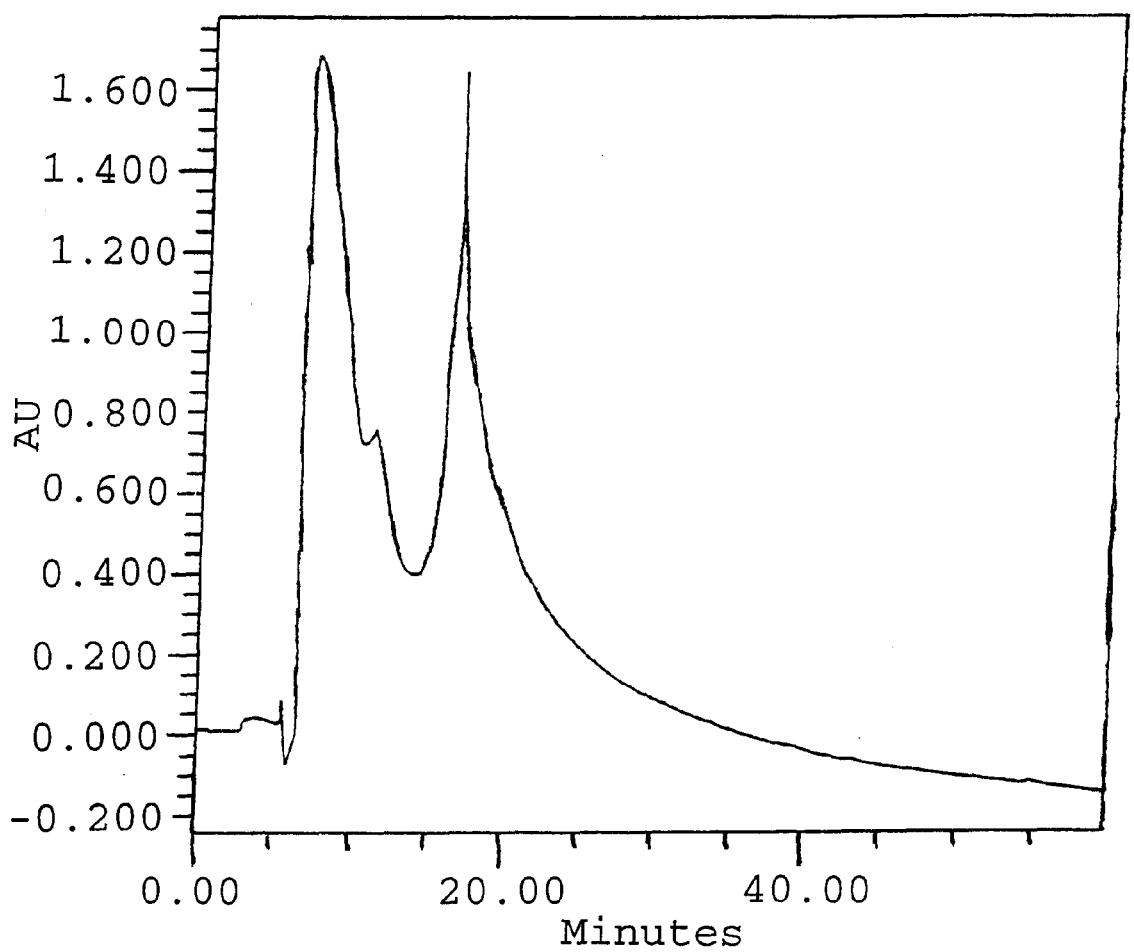
FIG. 10 shows the RP-HPLC (Vydac Polymer 259VHP54 column 4.6×25 mm) of 182 ng of MBPLM from the same MBPLM-containing tubes, fractions 10–13 from HPSEC in 0.1 M $NH_4OH$ (FIG. 9), as used for the separation demonstrated in FIG. 9 except that $NH_4OH$ was substituted with 0.1% acetic acid. As for the HPSEC fractionation using 0.1% acetic acid (see FIG. 7), two peaks were detected by UV monitoring at $A_{215}$ with neither having any MBPLM detected by RIA.

The RP-HPLC column (Vydac 259VHP54) is made of a polymer matrix and can be used with strongly alkaline conditions, such as 0.1 M $NH_4OH$. The MBPLM-containing fractions from the HPSEC column operated with 0.1 M $NH_4OH$ (FIG. 6) were dried down and dissolved in 200 ml of 0.1 M $NH_4OH$, which served a s Buffer A. Buffer B was 90% ACN in $dIH_2O$. After loading the sample on the column, the linear gradient elution was started with buffer "B" 0–50% introduced from 5 to 55 min. Further impurities were removed, and the MBPLM eluted as a single peak at 7–8 min (FIG. 9). An alternative fractionation was performed with the same column under the same conditions except that 0.1% acetic acid was substituted for 0.1 M $NH_4OH$. Two major separate peaks eluted at 7–8 and 16–17 min (FIG. 10). Similar to the influence of changing $NH_4OH$ to acetic acid for the HPSEC column (FIGS. 6 and 7), neither peak had any immunoreactivity for MBPLM by RIA.

EXAMPLE 34
Other Chromatographic Methods

MBPLM was not retained on any of the cation exchange columns even under conditions when $dIH_2O$ was used as the solution. mAbs 845D3 or F41, with defined reactivities to MBP peptides 80–89 and 80–85 in ELISA, respectively (50,35), were incapable of absorbing MBPLM from urine tested before passage over the Sep-pak combination (FIG. 2) or before $C_4$ RP-HPLC (FIG. 4) after multiple attempts using any of the affinity methods described or referenced above. This demonstrated that the affinity between the MBPLM and mAbs on the column or in solution with the disks was either too low or that the immunoreactivity of the polyclonal R110 antiserum, used in the RIA for MBPLM, was not simulated by the mAbs on the column. HPAEC was tried by applying the relative pure urinary MBPLM from RP-HPLC fractionation onto a Waters DEAE 5 PW with a gradient elution of 0–0.2 M ammonium acetate (pH 5.18) mixed with 10% methanol. MBPLM was readily eluted, but the yield was only 6%.

As an ion pair, TEAP resulted in a separation comparable to that when TEA was used, but TEAP is not volatile and its presence caused all molecular signals on ESMS to be suppressed by the phosphate salt. When TFA, an acidic ion pair commonly used in the separation of proteins and peptides by RP-HPLC, as well as HFBA or formic acid was used rather than TEA in the RP-HPLC on a $C_{18}$ column (FIG. 5), a marked reduction or loss of MBPLM immunoreactivity was observed. The mechanism for this effect is unclear, but could be due to strong hydrophobicity effects of the RP-HPLC for these acidic ion pairs with more discriminative separation of individually non-reactive components of MBPLM noted with other columns (FIGS. 7 and 10).

EXAMPLE 35

Structural Characterization

Amino acid analysis:

No consistent and interpretable results could be obtained to document the presence of amino acids in HPLC fractions containing MBPLM. After the step of HPSEC on a Waters Shodex Q801/S column using 0.1% acetic acid when there was loss of immunoreactivity for MBPLM (FIG. 7), amino acid analysis (performed by Mario Moscarello, M.D., Ph.D., of the Hospital for Sick Children in Toronto, Canada) revealed no clear and consistent composition. Therefore, the possibility of a modified amino acid(s) remaining in the hydrolyzed sample could not be excluded.

Amino acid sequencing:

Amino acid sequencing of MBPLM from the amino terminal failed to furnish any usable information about structure. The possibility of a blocked amino-terminal was considered as one of the explanations.

Mass Spectrometry:

A prominent signal at 187 was noted by ESMS in the negative mode, and with the expectation that a small MBP peptide would be found, viewed initially as a non-MBPLM urine component containing sulfate that might be suppressing other signals. Following sulfatase treatment or solvolysis with 40 mM $H_2SO_4$, the peak at 187 disappeared on ESMS as did the immunoreactivity for MBPLM. This led to a careful analysis of the 187 peak and a series of findings which, summarized as follows, indicated that the 187 mass in urinary MBPLM was cresol sulfate.

Figure 11A:
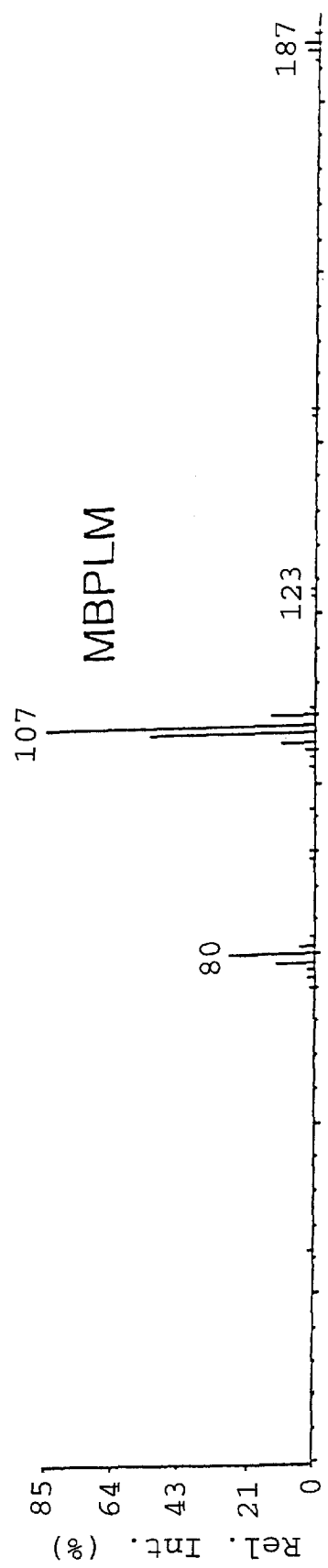
FIG. 11 shows the comparative spectra using ESMS in the negative mode followed by MS/MS for urinary MBPLM purified by RP-HPLC (fraction at 7–8 min in FIG. 9) (11A), p-cresol sulfate (11B), and p-cresol sulfonate (11C). Each material contained species at 80 and 107 mass units with the relative ratio of 80:107 being identical for p-cresol sulfate and urinary MBPLM, but different for p-cresol sulfonate. m-Cresol sulfate and o-cresol sulfate had molecular species identical to p-cresol sulfate.

1. Using the MBPLM isolated by the Vydac 259VHP54 column and 0.1 M $NH_4OH$ (FIG. 9), ESMS negative scans revealed a mass of 187 in fractions 7–8. After MS/MS, masses of 80 and 107 were apparent, with the height of the mass at 107 about 5 times the one at 80 (FIG. 11A).

Figure 11B:
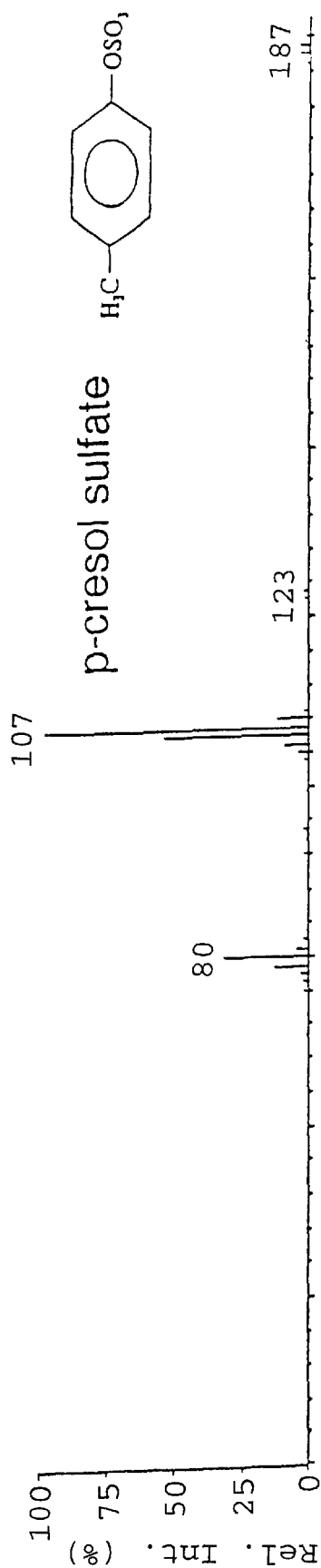
Figure 11C:
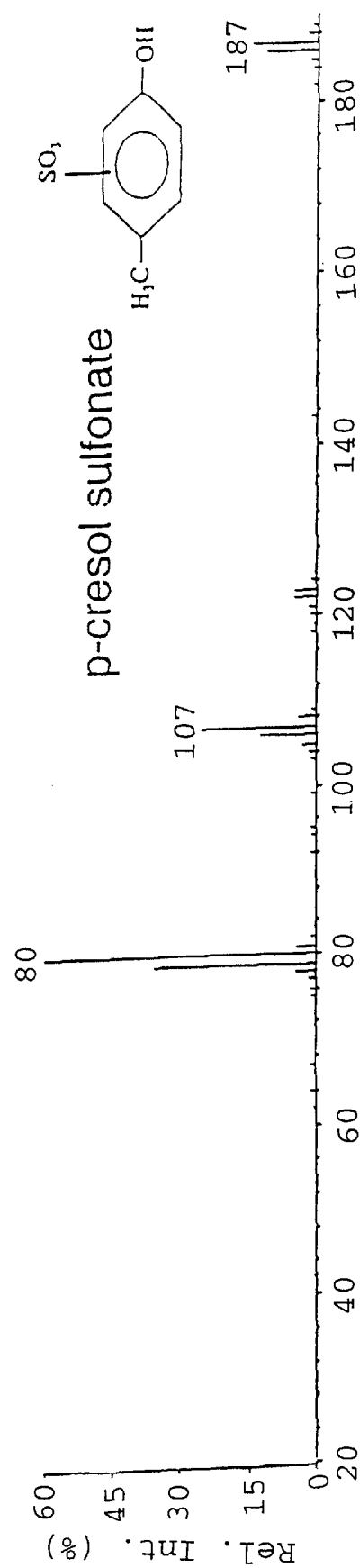

2. p-Cresol sulfate (FIG. 11B), m-cresol sulfate, and o-cresol sulfate were shown to have identical masses and ratios (FIG. 11B) as does MBPLM. The presumed structure of 80 is $SO_3^-$ and 107 is 4-methylphenol (with a loss of the H on the OH). p-Cresol sulfonate was also synthesized, but its appearance on ESMS and MS/MS did not conform (FIG. 11C) as did p-cresol sulfate, with the 187 mass and its fragments detected in the highly enriched fraction in urinary MBPLM.

Figure 12A:
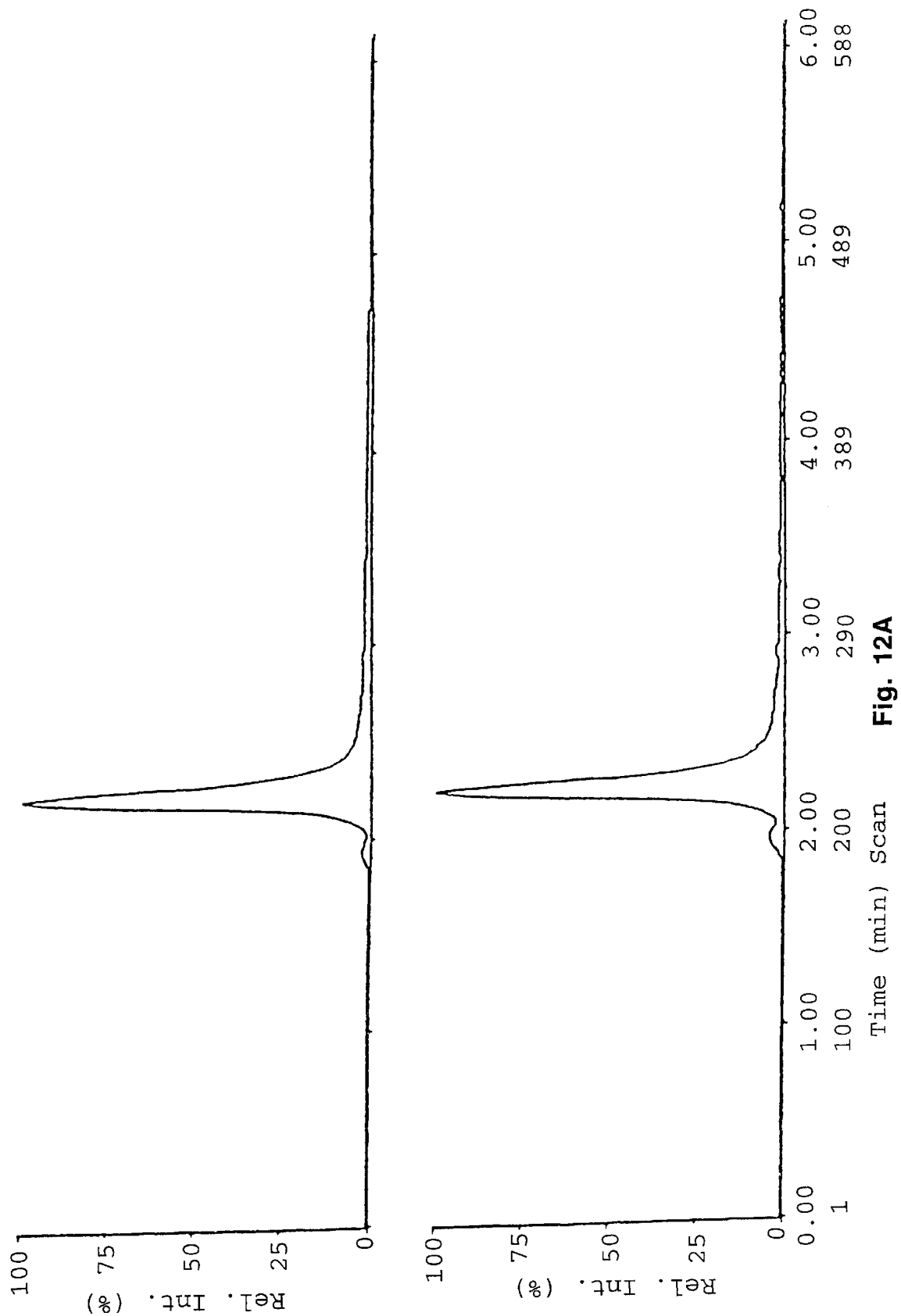
FIG. 12 shows the separation by HPLC (0.1% acetic acid and ACN in 0.1% acetic acid on a 4.6×100 mm C8 column with the flow rate of 1.0 ml/min) followed by MS/MS for MRM of 5 $\mu l$ of normal urine (12A) and 5 $\mu g$ of p-cresol sulfate (12B). Distinct peaks for p-cresol sulfate of 187/107 and 187/80 at 2.2 min were noted (12B), and these were identical to the peaks obtained for separation of MBPLM in unfractionated urine (12A).
Figure 12B:
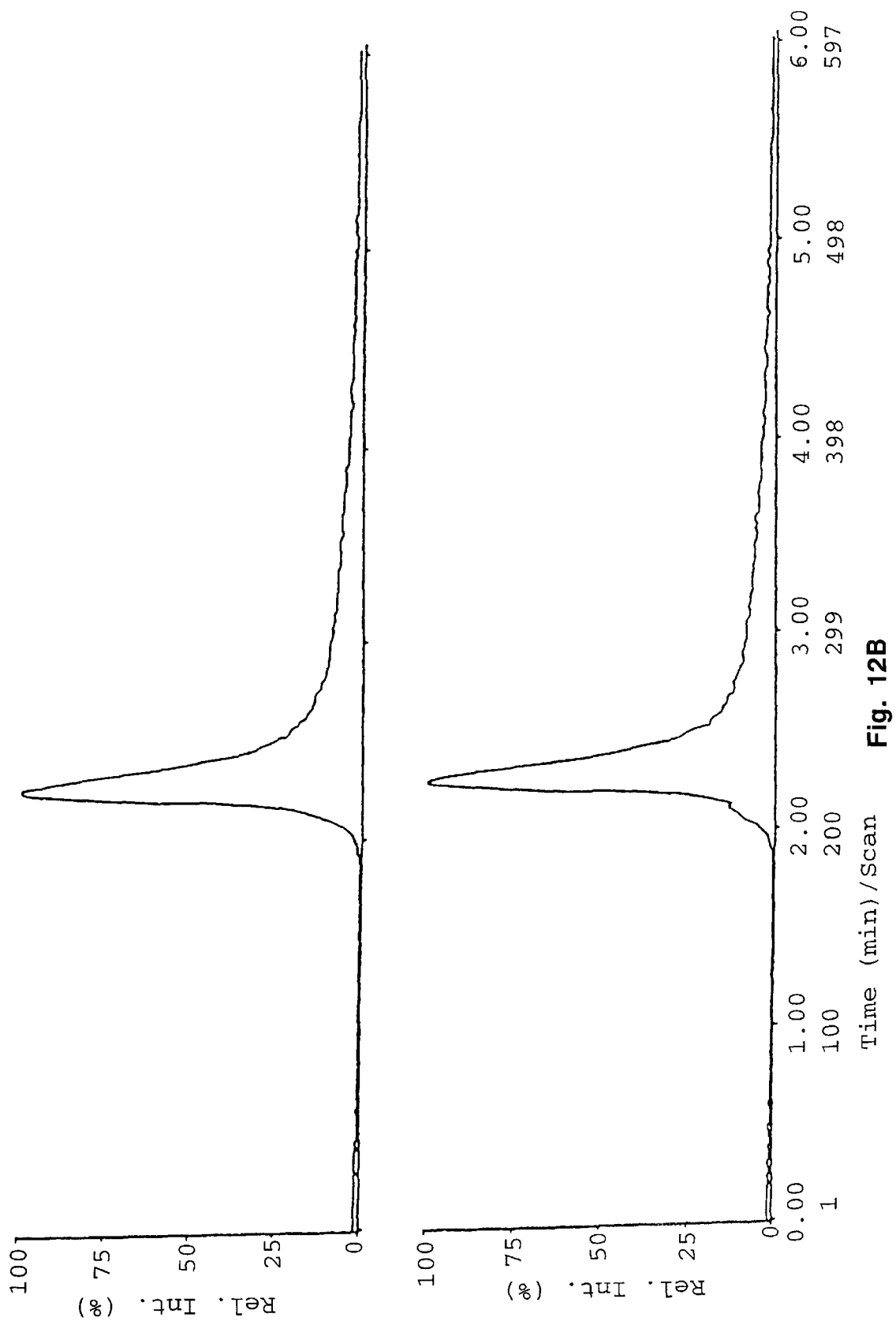

3. To add to the confidence of this identification, a urine specimen with minimal preparation (filtered through 0.22 μm filter only) and from a normal adult volunteer from another site and not part of the current urine collection was processed by MRM and showed by negative scanning masses to have fragments at 187/107 and 187/80 (FIG. 12A) eluted at the same time as p-cresol sulfate (FIG. 12B). These results indicated that the 187 mass had not been introduced as a contaminant during the lengthy preparative method for isolating urinary MBPLM.

4. When the polymer column was joined with the ESMS, the peak of 187 on negative scanning was in the second peak (FIG. 10). A dominant spectrum was not evident in the first peak.

EXAMPLE 36

Nuclear Magnetic Resonance

Figure 13:
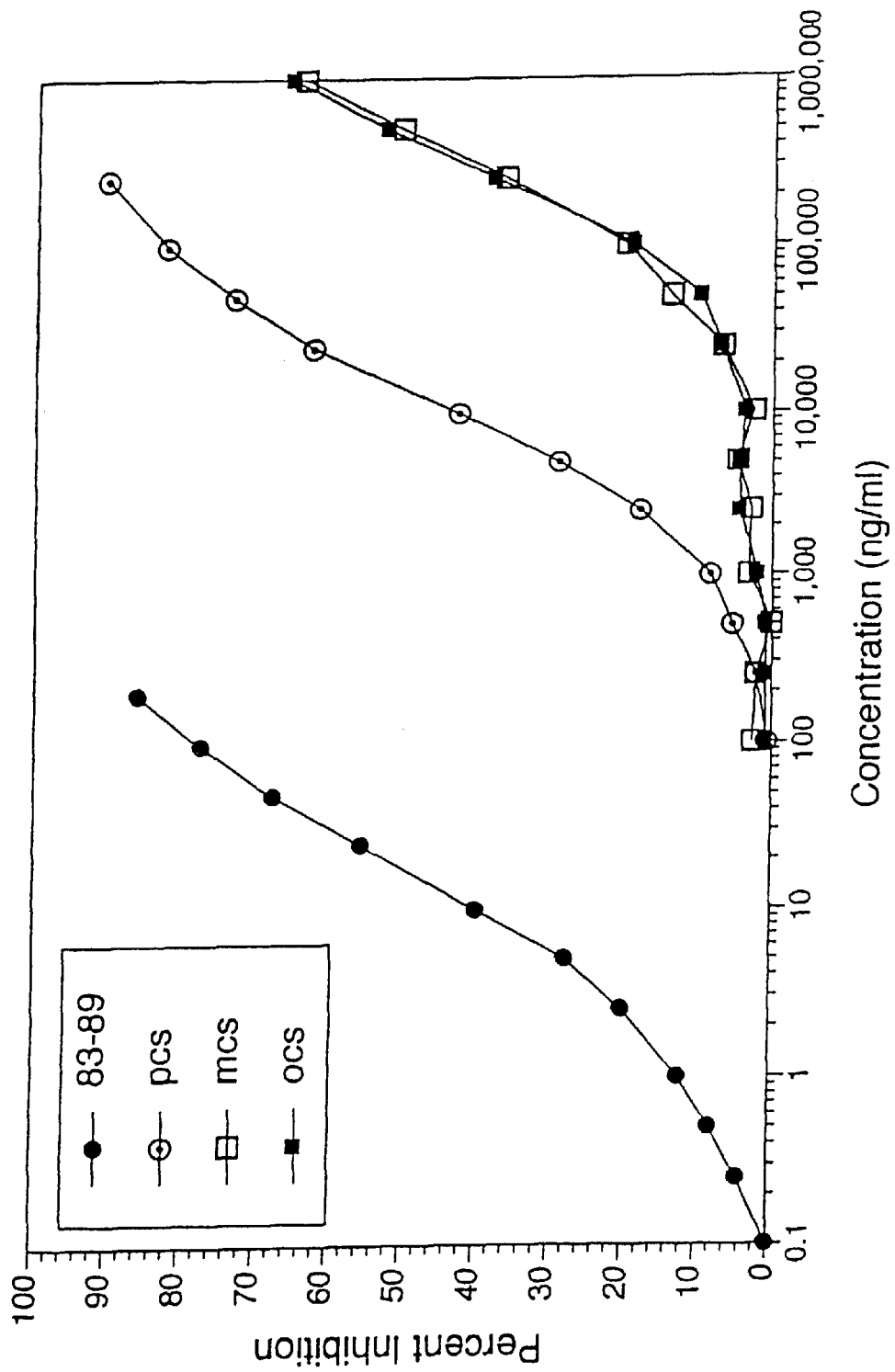
FIG. 13 shows the inhibition by MBP peptide 83–89 and p-cresol sulfate, m-cresol sulfate or o-cresol sulfate in RIA with R110 anti-MBP and radiolabeled MBP peptide 69–89. On a weight basis, p-cresol sulfate displaces the radioligand about 0.1% as much as MBP peptide 83–89 but in a parallel manner, implying similarity of epitopes recognized.

The $^1H$ (FIG. 13) and $^{13}C$ NMR spectra of purified urinary MBPLM and the three isomers of cresol sulfate were compared. In the aromatic region of $^1H$ spectra (FIG. 13), the $^1H$—$^1H$ coupling patterns can be used to identify the substitution patterns on benzene rings. The peak patterns of the sulfated compounds differs from o-, m- and p-cresols due to the presence of the sulfate group. $^1H$ spectra were also integrated, shown to contain the expected number of peaks, and only the aromatic ring peaks, the singlet for the $CH_3$ group, and a broad singlet for the H on the sulfate group were observed. Urinary MBPLM had the $^1H$ and $^{13}C$ NMR spectra identical to that of p-cresol sulfate, but different from m-cresol sulfate and o-cresol sulfate. Urinary MBPLM and p-cresol sulfate presented four peaks in the aromatic region of the $^{13}C$ spectra (120–160 ppm), while m-cresol sulfate and o-cresol sulfate revealed six peaks.

EXAMPLE 37

Immunochemical Studies of p-Cresol Sulfate

Figure 14:
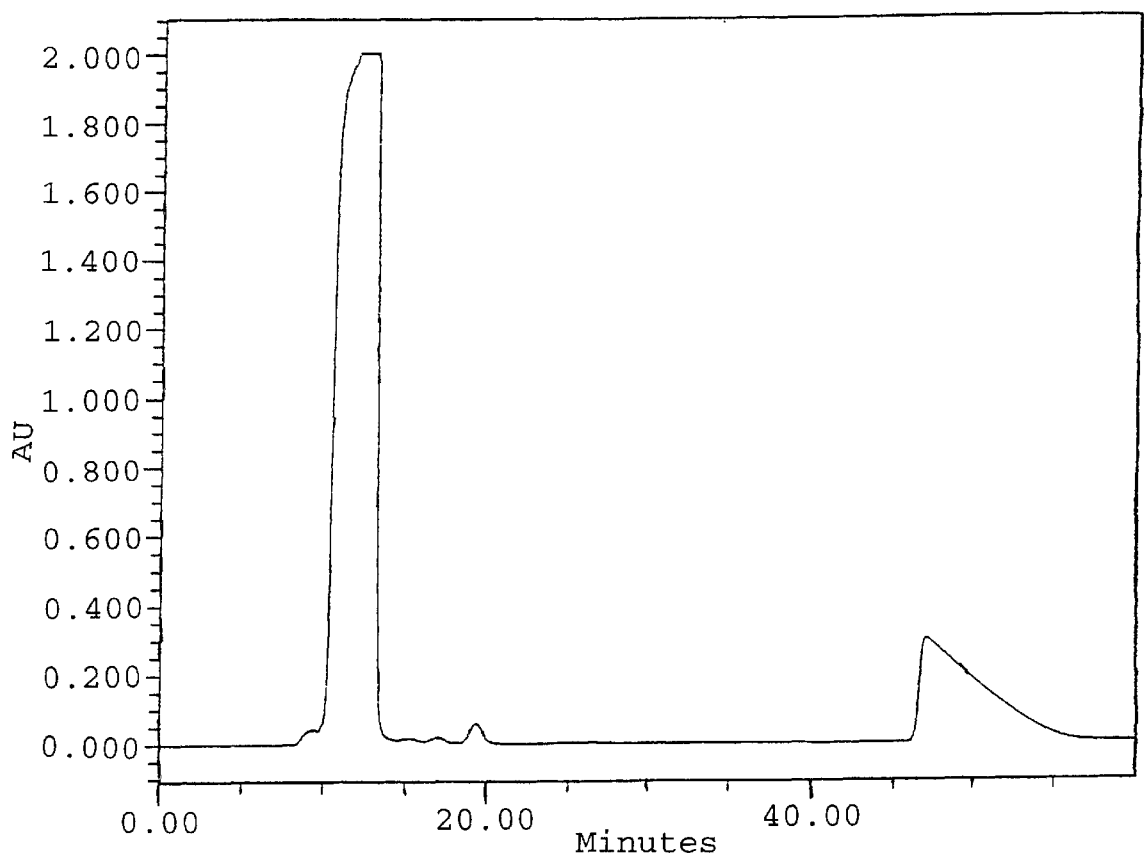
FIG. 14 shows the same column and conditions described for separating MBPLM (FIG. 6) and p-cresol sulfate was separated by HPSEC (Waters Shodex Q801/S column, 8×250 mm) in 0.1 M $NH_4OH$. p-Cresol sulfate eluted at 10–13 min.

The p-, m- and o- isomers of cresol sulfate were tested in the RIA used for detection of urinary MBPLM. The cresol sulfate isomers were stable when solubilized in a buffer consisting of 0.14 M NaCl, $4 \times 10^{-4}$ M MgSO4, $1.5 \times 10^{-4}$ M CaCl2, $10^{-2}$ M Tris buffer (pH 7.4) and 0.1% (w/v) BSA. p-Cresol sulfate functioned as an inhibitor in parallel with MBP peptide 83–89, the standard used in the RIA, but with a relative reactivity of 0.1%, or 1000-fold less (FIG. 13). m-Cresol sulfate and o-cresol sulfate reacted with similar levels but considerably less than p-cresol sulfate (FIG. 14). The reactivity of p-cresol sulfate alone by this RIA and the failure of p-cresol sulfate from the second peak of material isolated by HPLC (FIGS. 7 and 10) to react is probably based upon the lower concentration of p-cresol sulfate in the HPLC fractions. The restoration of reactivity on admixture of HPLC fractions at specific ratios (FIG. 8) presumably results from an increase in affinity of the antibody for p-cresol sulfate and another minor component of urinary MBPLM. p-Cresol, m-cresol, and o-cresol did not react in this RIA. When tested in the RIA for CSF MBPLM (49), which does not detect urinary MBPLM and which reacts with a different epitope of MBP (22), the p-cresol sulfate did not react.

EXAMPLE 38

Importance of the Sulfate-Containing Group

Upon sulfatase treatment (51) of purified MBPLM, a marked decrease in immunoreactivity occurred. This indicated that the $SO_3^-$ group was attached to the oxygen on the benzene ring and is consistent with its identity as a cresol sulfate and not a sulfonate (48). Upon solvolysis (52) with $H_2SO_4$, the peak at 187 disappeared, as did the immunoreactivity for MBPLM. This provides further evidence of the identity of the sulfate group and is consistent with the immunochemical findings that cresol failed to react in the RIA and was dissimilar to the MBPLM structure by MS.

EXAMPLE 39

Chromatographic Features of p-Cresol Sulfate

Figure 15:
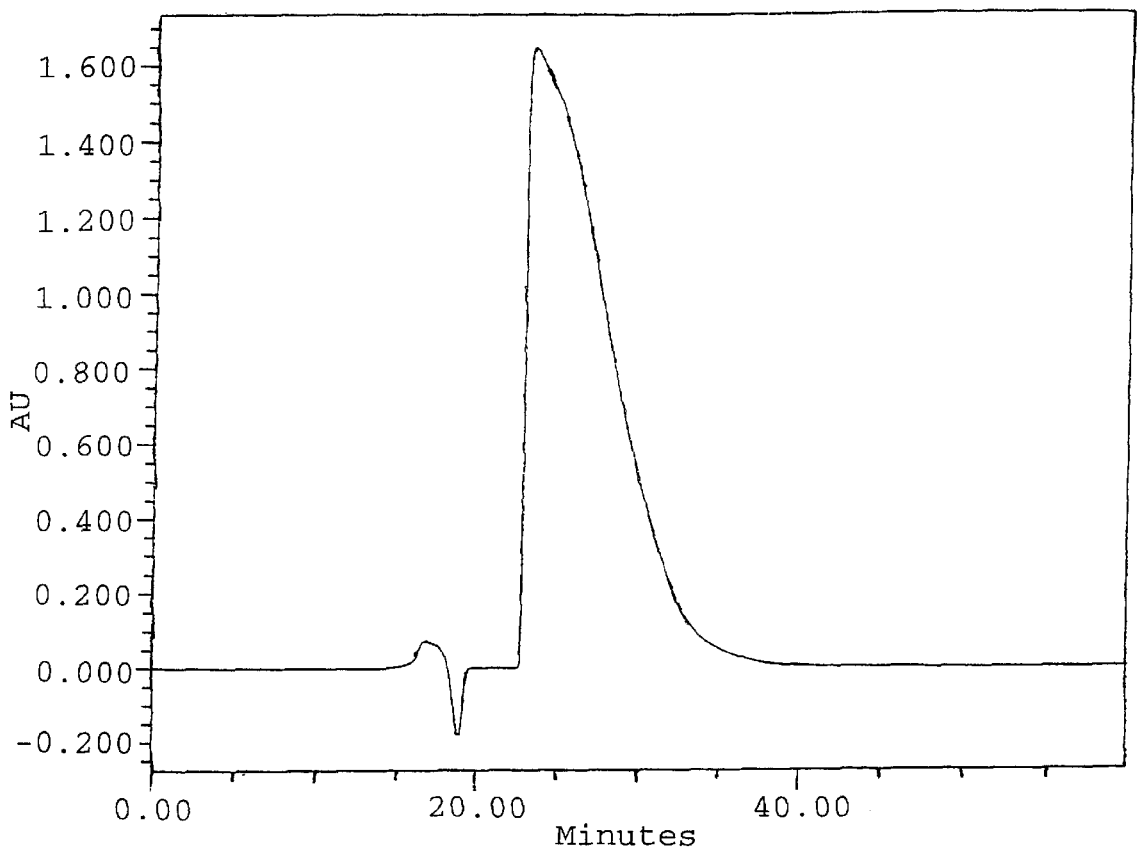
FIG. 15 shows the same column and conditions described for separating MBPLM (FIG. 7) and p-cresol sulfate was separated by HPSEC (Waters Shodex Q801/S column, 8×250 mm) in 0.1% acetic acid. p-Cresol sulfate eluted with a pattern identical to that of MBPLM.
Figure 16A:
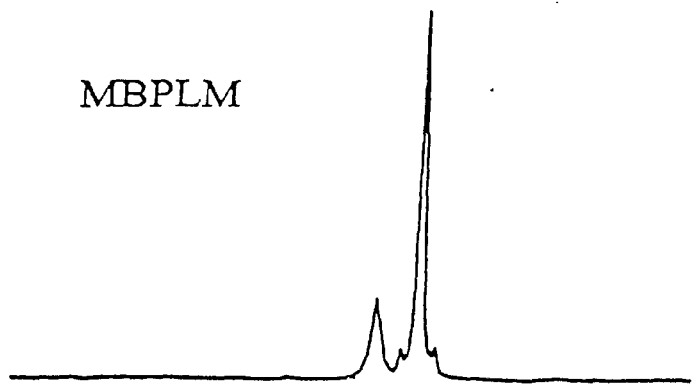
FIG. 16 shows the NMR elution profiles of MBPLM (16A), p-cresol sulfate (FIG. 16B), o-cresol sulfate (FIG. 16C) and m-cresol sulfate (FIG. 16D).
Figure 16B:
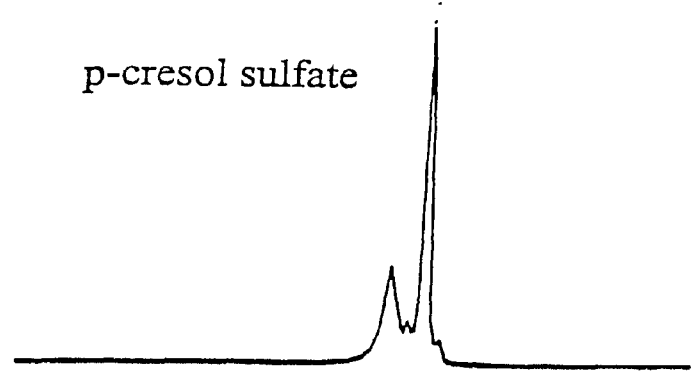
Figure 16C:
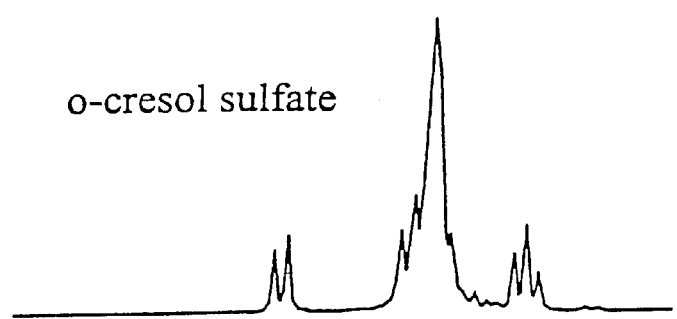
Figure 16D:
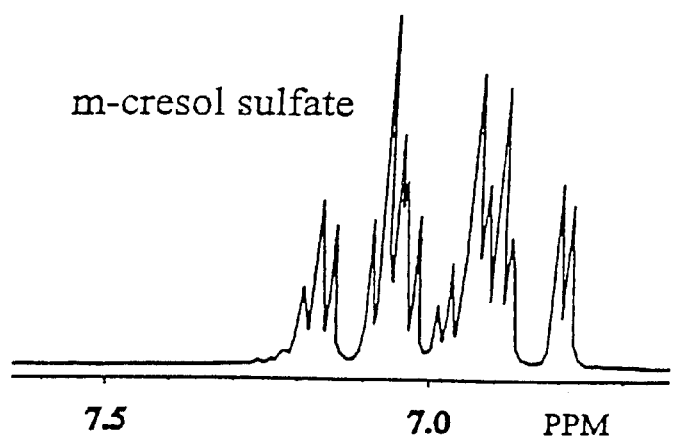

Confirming evidence of the identity that cresol sulfate was a dominant component of MBPLM was obtained by the following steps. First, all cresol sulfate isomers behaved on the Sep-pak separation (FIG. 2) with similar characteristics as MBPLM. Second, by HPSEC in 0.1 M $NH_4OH$, the same profile was obtained for p-cresol sulfate (FIG. 14) as for MBPLM (FIG. 6). Third, on the same column but in 0.1% acetic acid, a profile (FIG. 15) simulating that of MBPLM (FIG. 7) was evident with p-cresol sulfate.

p-Cresol Sulfate. Myelin Basic Protein-Like Material and Multiple Sclerosis

Evidence obtained from experiments described herein indicates that a major component of urinary MBPLM is p-cresol sulfate. This conclusion is based on a number of observations. First, purified MBPLM shows a peak of 187 on negative ESMS, which is the same spectral features as any of the three cresol sulfate isomers. Second, MBPLM and p-cresol sulfate have the same elution features by MRM. Third, the cresol sulfates have immunoreactivity in parallel with MBPLM in the RIA used for MBPLM detection. Fourth, p-cresol sulfate has the same properties on HPLC as does MBPLM. And fifth and most conclusive, both the $^1H$ and $^{13}C$ NMR spectra of urinary MBPLM and p-cresol sulfate are identical, but different than the spectra for m-cresol sulfate and o-cresol sulfate.

Though different in sensitivity and discrimination, the combination of immunochemical, chemical and structural analyses is internally consistent in the identification of p-cresol sulfate as the major component of urinary MBPLM. By ESMS and MS/MS, the three isomers and urinary MBPLM had the same peaks. NMR provided the most definitive means for structural characterization and identification or urinary MBPLM as p-cresol sulfate. In the NMR $^1H$ spectra, the $^1H$—$^1H$ coupling leads to different peak patterns, and these patterns can be used to characterize the substitutions on a n aromatic ring (64). In the case of the three isomers of cresol sulfate, the patterns do not resemble the expected patterns (i.e., the AA'BB' pattern for the p-substituted ring) due to the influence of the sulfate group. However, the peak pattern of the p-, m- and o- sulfated cresols are quite distinct and allow for easy identification of the p-isomer in MBPLM. $^{13}C$ NMR offers a much greater dispersion due to the larger ppm range, and the chemical shifts are especially sensitive to the local environment (65). The $^{13}C$ spectra of the m- and o-isomers displayed six peaks in the aromatic region of the spectra (120–160 ppm), but, due to the internal plane of symmetry, the p-isomer had only four peaks in this region.

Although the detection of MBPLM in urine met the immunochemical requirements for a valid and reliable RIA, prior to the results reported herein, it continued to be necessary to use the additional label of "-like material", because there was no independent confirmation by bioassay or chemical characterization that definitively identified the immunoreactive material as a MBP peptide. The results of the present study reveal that what is detected by an RIA to be immunoreactive with an antibody and give the appearance of displacing the radioligand may do so by means other than being similar in primary sequence to the radioligand. The combined immunochemical and structural data of the present invention indicate that the immunochemical cross-reactivity between the cryptic epitope of MBP peptide 83–89, previously shown to have helical structure unusual for a small peptide (66), and p-cresol sulfate results from a sharing of conformation.

Urinary MBPLM was previously demonstrated to have a size of less than 1000, or even 500, daltons (22), and in the present investigation, it was shown to be hydrophilic and acidic. However, the discovery of p-cresol sulfate as a major component of MBPLM was unanticipated. In fact, the strategy and planning for isolating MBPLM was based on its being a noncryptic epitope in MBP peptide 80–89, and probably peptide 83–89, recognized by antiserum R110 in the RIA for urine MBPLM (22, 23) with a more complex conformation than expected for a small peptide of its predicted size (40). This led to the initial reliance on immunoaffinity procedures and a search for a peptide with a mass between 822 Da, that of MBP peptide pyro83–89, and 1184 Da, which is characteristic for MBP peptide 80–89. Once dependable HPLC procedures (as monitored by RIA) were established for purifying MBPLM, it became evident that the elution of MBPLM on any of the HPLC systems was different from any peptide that could arise from within MBP peptide 80–89.

Although p-cresol sulfate fulfills the criteria for being a major component of urinary MBPLM, it seems likely that at least one more component is in urinary MBPLM and influences its sensitive detection. It is postulated that another small molecule, present in trace amounts, might stabilize the p-cresol sulfate and enhance, or restore (FIG. 8) its affinity for the polyclonal antibody recognizing the cryptic determinant in MBP peptide 83–89. Related to the estimated mass of MBPLM of 500–1000 Da, only molecule(s) of 300–700 Da would be expected. The ES/MS and NMR spectra reveal no other major peaks. Some guidance as to what the additional factor(s) in MBPLM are may be derived from the behavior of urinary MBPLM during its isolation. Passage of MBPLM-containing fractions on a HPLC $C_{18}$ column with acidic ion pairs resulted in near total loss of immunoreactivity of MBPLM. However, when TEA was used, the yield was excellent. When fractionated on phenyl or $C_4$ HPLC columns or on a Sep-pak $tC_{18}$ column using TFA or on a $C_{18}$ HPLC column without an ion pair, MBPLM was retained poorly but recovered well. Fractionation of relatively pure MBPLM under strongly alkaline conditions on Waters Shodex Q801/S HPSEC column with potent selection of small molecules showed a single peak of immunoreactivity (FIG. 6), but the same column used with 0.1% acetic acid show two peaks with no immunoreactivity (FIG. 7). However, by admixing the two peaks at selected ratios, MBPLM immunoreactivity could be restored (FIG. 8) with a yield of over 90%. A similar phenomenon occurred during RP-HPLC on the Vydac 259VHP54 polymer column with which a single peak with MBPLM immunoreactivity appeared when using a solution of 0.1 M $NH_4OH$ (FIG. 9), and two peaks lacking immunoreactivity were present when 0.1% acetic acid was used (FIG. 10). These results indicate the existence of at least two different molecules, bound together by labile bonds which are susceptible to acidic, but not basic, conditions and are critical to the immunoreactivity of urinary MBPLM. The known lability of the sulfate bond in p-cresol sulfate to an acidic environment could explain the loss, but not the restoration, of immunoreactivity.

With the identification of p-cresol sulfate as the dominant entity of urinary MBPLM, the investigative aim shifts from examining the catabolism of MBP to a delineation of the source of p-cresol sulfate, the form(s) in which it exist in tissues and fluids of the body and its further relationship to the pathobiology and clinical disability of MS. The best known source of p-cresol is coal tar (53), but its source in the body or in body fluids is unknown. p-Cresol is presumably derived from tyrosine residues, a source not likely for m-cresol or o-cresol. The best known source of p-cresol in the human body is from the tyrosine residues in proteins through the action of colonic bacteria, which generate volatile phenolic compounds excreted in the urine (54). In the urine, p-cresol concentrations are considerably higher than that of either m-cresol or o-cresol.

In vivo, p-cresol sulfate has only one known source, tyrosine sulfate. Sulfotransferases (59) are widespread, and tyrosine sulfation is the most abundant post-translational modification of tyrosine residues in multicellular organisms (66). It occurs in many soluble proteins passing through secretory pathways (66) and is also present in membrane proteins (67). The phenolic hydroxyl group of tyrosine is considered to be the only sulfation site on a peptide chain (68). There are four tyrosine residues, located at position 14, 69, 127 and 134 in human MBP (69), but none is located near MBP peptide 80–89. Also, none is known to be sulfated; however, the acid lability of the tyrosine-o-sulfate under acidic conditions (68) would prevent sulfated tyrosine from being detected by conventional amino acid analysis after acid hydrolysis. It is also possible that the p-cresol sulfate has a source independent of MBP. As a source for p-cresol sulfate, tyrosine sulfate is in proteins, such as CD44, a transmembrane glycoprotein which binds many molecules (70), and CD62P, which mediates the adhesion of T lymphocytes to P-selectin (71), potentially involved in the CNS tissue injury in MS. Tyrosine sulfate is a known component of urine, in which it has recently been characterized to exist as an L-p-tyrosine isomer (72).

Molecular mimicry is used to describe the sharing of immunological recognition of two different molecules by the same cell or reagent. Immunoglobulin products of B cells are typically capable of detecting small structural differences in MBP peptides (22, 44, 45). Thus, the unexpected cross-reactivity of an MBP peptide and a nonpeptide, such as p-cresol sulfate, indicates that the distance in structure covered by immunological cross-reactivity can be broad. For cellular reactions, molecular mimicry has been postulated as the basis of autoimmune responses by autoreactive T cells generated by epitopes of infectious agents that 'mimic' or share epitopes with an autoantigen (73). T cell responses to MBP are highly degenerate (62, 74) and permit cross-reactivities with only minimal sharing of structures which can activate responsive T cells. A mechanism by which p-cresol sulfate can influence the immune response or other biological events is unknown, but sulfur-containing drugs can activate sensitized T cell clones through the T cell receptor (63). The present invention identifies p-cresol sulfate in urine, and as with MBPLM, provides a relationship between p-cresol sulfate levels and clinical changes in MS.

The following references were cited herein:
1. Anderson et al., *Ann Neurol* 1992;31:333–336
2. Weinshenker et al., *Neurologic Clinics* 1995;13:119–146
3. Weinshenker et al., *Brain* 1989;112:1419–1428
4. Runmarker et al., *Brain* 1993;116:117–134
5. Paty et al., In: Rudick RA, Goodkin DE, eds. *Treatment of Multiple Sclerosis: Trial Design Results and Future Perspectives*. London: Springer-Verlag, 1992:47–90
6. Rodriguez et al., *Neurology* 1994;44:28–33
7. Goodkin et al., *Arch Neurol* 1989;46:1107–1112
8. Weinshenker et al., *Can J Neurol Sci* 1987;14:255–261
9. Runmarker et al., *J Neurol* 1994;241:385–390
10. Sharief et al., *N Engi J Med* 1991;325:467–472
11. Noseworthy et al., *Neurology* 1993;4 3:A355
12. Paty et al., *Neurology* 1993;43:662–667
13. Filippi et al., *Neurology* 1994;44:635–641
14. Franket al., *Ann Neurol* 1994; 36(Su pl):S86–S90
15. Thompson et al., *Br Med J* 1990;300:631–634
16. Gass et al., *Ann Neurol* 1994;36:62–67
17. Morell et al., In: Siegel et al., eds. *Basic Neurochemistry*. 4th ed. NY: Raven Press, 1994:117–143
18. Cohen et al., *N Engl J Med* 1976;295:1455–1457
19. Whitaker, J N, *Neurology* 1977;27:911–920
20. Whitaker, J N et al., *Ann Neurol* 1993;33:10–17
21. Whitaker, J N et al., *Ann Neurol* 1993;34:273
22. Whitaker, J N et al., *Ann Neurol* 1987;22:648–655
23. Whitaker, J N et al., *Ann Neurol* 1994;35:577–585
24. The IFN Multiple Sclerosis Study Group. *Neurology* 1993;43:655–661
25. Kurtzke J F. *Neurology* 1983;33:1444–1452
26. Sipe et al., *Neurology* 1984;34:1368–1372
27. Reder et al., *J Interferon Res* 1992;12:195–198
28. Ostle, M., *Statistics in Research*. 4th ed. Ames: The Iowa State University Press, 1988
29. Snedecor et al., *Statistical Methods*. 7th ed. Ames: The Iowa State University Press, 1980
30. Draper N R, Smith H. *Applied Regression Analysis*. 2nd ed. New York: John Wiley & Sons, 1966
31. Daniel W W. *Applied Nonparametric Statistics*. Boston: Houghton Mifflin, 1978
32. Prentice RL. *Biometrika* 1978;65:167–179
33. Cox D R. *J Roy Statist Soc, Series B* 1972;34:187–220
34. Montgomery D C. *Design and analysis of experiments*. 2nd ed. New York: John Wiley & Sons, 1984:192–214
35. Whitaker, J N et al., *J Neuroimmunol* 1994;52:53–60
36. Whitaker, J N et al., *Ann Neurol* 1980;7:58–64
37. Bashir et al., *Neurology* 1980;30:1184–1192
38. Whitaker, J N et al., *Neurology* 1983;33:744–749
39. Mirsky et al., *J Cell Biol* 1980;84:483–494
40. Whitaker, J N et al., *J Neurochem* 1990;55:568–576
41. Campagnoni et al., *J. Biol. Chem.* 1993;268:4930–4938
42. Campagnoni, A T, *J. Neurochem.* 1988;51:1–14
43. Moscarello, M A (ed) (1990) *Myelin basic protein: A dynamically changing structure* Vol. 336. Dynamic Interactions of Myelin Proteins. Eds. Hashim, et al., Wiley & Sons, Inc., New York
44. Day, ED & Potter, NT, *J. Neuroimmunol.* 1986;10:289–312
45. Whitaker, J N et al., *J. Exp. Med.* 1977;146:317–331
46. Lublin, F D & Reingold, S C, *Neurology* 1996;46:907–911
47. Whitaker, J N et al., *Ann. Neurol.* 1995;38:625–632
48. Coward et al., *Clin. Chim. Acta* 2 1996;47:121–142
49. Whitaker, J N & Herman, PK *J. Neuroimm.* 1988;19:47–57
50. Price, J O et al., *J. Immunol.* 1986;136:2426–2431
51. Fowler, L R & Rammler, D H, *Biochemistry* 1964;3:230–237
52. Scommegna, et al., *J. Clin. Endocrin. Metab.* 1971;33:787–792
53. Merck Index. (1976), 9th Ed., pp. 335, Merck & Co., Inc., Rahway, N.J.
54. Geypens, B et al., *Gut* 1997;41:70–76
55. Percy, A K et al., *Neurology* 1998;51:1339–1341
56. Whitaker, J N, *Mult. Scler.* 1998;4:16–21
57. Bashir, K B & Whitaker, J N, *Neuro. Net. Com.* 1998;2:162–166
58. Dills, R L et al., *J. Chromatography* 1997;703:105–113
59. Falany, C N, *FASEB J.* 1997;11:206–216
60. Vainiotalo, S et al., *Toxicology* 1987;44:31–44

61. Morgan, J P & Penovich, P, *Arch. Neurol.* 1978;35:530–532
62. Hemmer, B, et al., *J. Exp. Med.* 1997;185:1651–1659
63. von Greyerz, S et al., *J. Immunol.* 1999;162:595–602
64. Levy G C et al., (1993) *Carbon-13 Nuclear Magnetic Resonance Spectroscopy*, Krieger Publishing Co., Malabar, Fla.
65. Lambert, J B et al., (1998) *Organic Structural Spectroscopy*, Prentice-Hall, Inc., Upper Saddle River, N.J.
66. Niehrs, C et al., *Chem.-Biol. Interact.* 1994;92:257–271
67. Hille, A & Huttner, W B, *Eur. J. Biochem.* 1990;188:587–596
68. Yagami, T et al., *Rapid Comm. Mass. Spect.* 1995;9:1335–1341
69. Scoble, H et al., *J. Neurochem.* 1986;47:614–616
70. Sleeman, J P et al., *Eur. J. Biochem.* 1998;255:74–80
71. Lim, Y -C et al., *J. Immunol.* 1998;161:2501–2508
72. Ranasinghe, J G et al., *Biosci. Biotech. Biochem.* 1999;63:229–231
73. Fujinami, R S & Oldstone, MBA *Science* 1985;230
74. Gran, B et al., *Ann. Neurol.* 1999;45:559–567

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of predicting the transition from relapsing-remitting multiple sclerosis to progressive multiple sclerosis in a patient with multiple sclerosis, comprising the steps of:
    (a) collecting multiple urine samples over time from a patient with multiple sclerosis;
    (b) measuring the amount of p-cresol sulfate in said urine samples; and
    (c) comparing said amount of said p-cresol sulfate in each urine sample from said patient to an art-accepted standard;
    wherein an increase over time in said urinary p-cresol sulfate levels in said urine samples is predictive of said transition from said relapsing-remitting multiple sclerosis to said progressive phase of multiple sclerosis in said patient.

2. The method of claim 1, wherein said measuring said p-cresol sulfate is by means selected from the group consisting of a radioimmunoassay, NMR spectroscopy, electrospray spectrometry and tandem mass spectrometry.

3. The method of claim 2, wherein said radioimmunoassay is a double-antibody radioimmunoassay.

4. The method of claim 3, wherein said double-antibody radioimmunoassay uses (1) rabbit antiserum directed towards an immunogen comprising a 30:70 mixture of bovine myelin basic protein residues 45–89 and bovine myelin basic protein residues 43–88, wherein said antiserum is specific for myelin basic protein-like material and recognizes a cryptic epitope in myelin basic protein consisting essentially of myelin basic protein residues 80–89, (2) radioiodinated human myelin basic protein residues 69–89 as a radioligand, (3) human myelin basic protein residues 83–89 as a radioimmunoassay standard and (4) goat anti-rabbit IgG as a second antibody.

5. The method of claim 1, wherein said art-accepted standard for said comparison is selected from the group consisting of urinary creatinine levels in each said sample, urinary volume of each said sample and total urinary volume collected over a defined period of time.

6. The method of claim 5, wherein said defined period of time is 24 hours.

7. A method of predicting an increase in the amount of lesions and total lesion area of a patient with multiple sclerosis, comprising the steps of:
    (a) collecting multiple urine samples over time from a patient with multiple sclerosis;
    (b) measuring the amount of p-cresol sulfate in said urine samples; and
    (c) comparing said amount of said p-cresol sulfate in each urine sample from said patient to an art-accepted standard; wherein an increase in said p-cresol sulfate level in said urine samples is predictive of an increase in the amount of lesions and/or total lesion area in said patient.

8. The method of claim 7, wherein said measuring said p-cresol sulfate is by means selected from the group consisting of a radioimmunoassay, NMR spectroscopy, electrospray spectrometry and tandem mass spectrometry.

9. The method of claim 8, wherein said radioimmunoassay is a double-antibody radioimmunoassay.

10. The method of claim 9, wherein said double-antibody radioimmunoassay uses (1) rabbit antiserum directed towards an immunogen comprising a 30:70 mixture of bovine myelin basic protein residues 45–89 and bovine myelin basic protein residues 43–88, wherein said antiserum is specific for myelin basic protein-like material and recognizes a cryptic epitope in myelin basic protein consisting essentially of myelin basic protein residues 80–89, (2) radioiodinated human myelin basic protein residues 45–89, or fragments thereof, as a radioligand, (3) human myelin basic protein residues 83–89 as a radioimmunoassay standard and (4) goat anti-rabbit IgG as a second antibody.

11. The method of claim 7, wherein said art-accepted standard for said comparison is selected from the group consisting of urinary creatinine levels in each said sample, urinary volume of each said sample and total urinary volume collected over a defined period of time.

12. The method of claim 11, wherein said defined period of time is 24 hours.

13. A method of predicting normal age-related changes in myelination on in a developing child, comprising the steps of:
    (a) collecting multiple urine samples over time from a child;
    (b) measuring the amount of p-cresol sulfate in said urine samples; and
    (c) comparing the amount of said p-cresol sulfate in each urine sample from said child to an art-accepted standard;
    wherein from birth through approximately one year of age, the amount of urinary p-cresol sulfate is lower in said child relative to established values for adults;
    wherein from approximately one year of age through approximately five years of age, the amount of urinary p-cresol sulfate in said child increases linearly exceeding said established values for adults; wherein between approximately five years of age and approximately eight years of age, the amount of urinary p-cresol sulfate in said child decreases to approximately established values for adults, wherein said amount of urinary p-cresol sulfate in said child is predictive of normal age-related changes in said developing child.

14. The method of claim 13, wherein said measuring said p-cresol sulfate is by means selected from the group consisting of a radioimmunoassay, NMR spectroscopy, electrospray spectrometry and tandem mass spectrometry.

15. The method of claim 14, wherein said radioimmunoassay assay is a double-antibody radioimmunoassay.

16. The method of claim 15, wherein said double-antibody radioimmunoassay uses (1) rabbit antiserum directed towards an immunogen comprising a 30:70 mixture of bovine myelin basic protein residues 45–89 and bovine myelin basic protein residues 43–88, wherein said antiserum is specific for myelin basic protein-like material and recognizes a cryptic epitope in myelin basic protein consisting essentially of myelin basic protein residues 80–89, (2) radioiodinated human myelin basic protein residues 69–89 as a radioligand, (3) human myelin basic protein residues 83–89 as a radioimmunoassay standard and (4) goat anti-rabbit IgG as a second antibody.

17. The method of claim 13, wherein said art-accepted standard for said comparison is selected from the group consisting of urinary creatinine levels in each said sample, urinary volume of each said sample and total urinary volume collected over a defined period of time.

18. The method of claim 17, wherein said defined period of time is 24 hours.

19. he method of claim 13, wherein said child has a demyelinating condition.

* * * * *

UNITED STATES PATENT AND TRADEMARK OFFICE
CERTIFICATE OF CORRECTION

PATENT NO.   : 6,284,473 B1
DATED        : September 4, 2001
INVENTOR(S)  : Whitaker et al.

It is certified that error appears in the above-identified patent and that said Letters Patent is hereby corrected as shown below:

Column 1,
Line 13, please insert the following paragraph before "Background of the Invention".

-- FEDERAL FUNDING
    This invention was produced in part using funds obtained through grant number NS23240 from the National Institutes of Health. Consequently, the federal government has certain rights in this invention. --

Signed and Sealed this

Twenty-fourth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.   : 6,284,473 B1
DATED        : September 4, 2001
INVENTOR(S)  : John N. Whitaker et al.

It is certified that error appears in the above-identified patent and that said Letters Patent is hereby corrected as shown below:

<u>Column 1,</u>
Line 4, please insert the following paragraph:
-- Federal Funding Legend
   The present invention was created in part using federal funds under NIH grant NS23240. Accordingly, the U.S. government has certain rights in this invention. --

Signed and Sealed this

Fifth Day of August, 2003

JAMES E. ROGAN
*Director of the United States Patent and Trademark Office*